(12) United States Patent
Mahurkar

(10) Patent No.: US 8,167,820 B2
(45) Date of Patent: May 1, 2012

(54) RETRACTABLE NEEDLE-SAFETY BLOOD SAMPLING DEVICE

(76) Inventor: Sakharam D. Mahurkar, Aurora, IL (US)

( * ) Notice: Subject to any disclaimer, the term of this patent is extended or adjusted under 35 U.S.C. 154(b) by 143 days.

(21) Appl. No.: 12/476,673

(22) Filed: Jun. 2, 2009

(65) Prior Publication Data
US 2010/0241029 A1    Sep. 23, 2010

Related U.S. Application Data

(60) Provisional application No. 61/162,096, filed on Mar. 20, 2009.

(51) Int. Cl.
*A61B 5/00* (2006.01)
(52) U.S. Cl. ........................................ 600/577
(58) Field of Classification Search ............... 600/577, 600/576; 604/92, 187; 29/428
See application file for complete search history.

(56) References Cited

U.S. PATENT DOCUMENTS

| | | | |
|---|---|---|---|
| 4,170,993 A | 10/1979 | Alvarez | |
| 4,562,844 A | 1/1986 | Carpenter et al. | |
| 4,631,057 A | 12/1986 | Mitchell | |
| 4,643,199 A | 2/1987 | Jennings, Jr. et al. | |
| 4,643,200 A | 2/1987 | Jennings, Jr. | |
| 4,655,751 A | 4/1987 | Harbaugh | |
| 4,693,708 A | 9/1987 | Wanderer et al. | |
| 4,702,738 A | 10/1987 | Spencer | |
| 4,725,267 A | 2/1988 | Vaillancourt | |
| 4,737,144 A | 4/1988 | Choksi | |
| 4,738,663 A | 4/1988 | Bogan | |
| 4,740,205 A | 4/1988 | Seltzer et al. | |
| 4,747,831 A | 5/1988 | Kulli | |
| 4,758,231 A | 7/1988 | Haber et al. | |
| 4,787,891 A | 11/1988 | Levin et al. | |
| 4,790,827 A | 12/1988 | Haber et al. | |
| 4,813,426 A | 3/1989 | Haber et al. | |
| 4,813,940 A | 3/1989 | Parry | |
| 4,834,717 A | 5/1989 | Haber et al. | |

(Continued)

FOREIGN PATENT DOCUMENTS

EP    0 539 634    5/1993

(Continued)

OTHER PUBLICATIONS

European Search Report, Application EP 10157073, Dated Jun. 25, 2010 (6 pages).

(Continued)

*Primary Examiner* — Max Hindenburg
*Assistant Examiner* — Fangemonique Smith
(74) *Attorney, Agent, or Firm* — Nixon Peabody LLP

(57) ABSTRACT

A safety device is presented for securely stowing a double sharp-ended needle. The device comprises a tubular adapter with a longitudinally-elongated channel. A needle holder is located in the channel to move from a distal orientation, in which one needle end projects from a distal adapter opening, and a proximal orientation, in which both needle ends are enclosed within the adapter body. A top plate transitions from a distal orientation, in which the plate is distal from a proximal adapter opening, and a proximal orientation, in which the top plate obstructs the proximal adapter opening. An actuator plate is attached to the adapter body to transition from a first position where the actuator plate retains the needle holder and top plate in distal orientations, and a second position where the needle holder and top plate move to proximal orientations.

35 Claims, 13 Drawing Sheets

U.S. PATENT DOCUMENTS

| | | | |
|---|---|---|---|
| 4,838,863 A | 6/1989 | Allard et al. | |
| 4,838,869 A | 6/1989 | Allard et al. | |
| 4,841,985 A | 6/1989 | Wanamaker | |
| 4,842,587 A | 6/1989 | Poncy | |
| 4,850,374 A | 7/1989 | Diaz-Ramos | |
| 4,892,107 A | 1/1990 | Haber | |
| 4,894,055 A | 1/1990 | Sudnak | |
| 4,904,242 A | 2/1990 | Kulli | |
| 4,923,447 A | 5/1990 | Morgan | |
| 4,932,418 A | 6/1990 | Coburn | |
| 4,947,863 A | 8/1990 | Haber et al. | |
| 4,966,593 A | 10/1990 | Lennox | |
| 4,984,580 A | 1/1991 | Wanamaker | |
| 4,988,339 A | 1/1991 | Vadher | |
| 4,994,034 A | 2/1991 | Botich et al. | |
| 5,019,044 A * | 5/1991 | Tsao | 604/110 |
| 5,030,209 A | 7/1991 | Wanderer et al. | |
| 5,046,508 A | 9/1991 | Weissler | |
| 5,049,133 A | 9/1991 | Pascual | |
| 5,049,136 A | 9/1991 | Johnson | |
| 5,053,010 A | 10/1991 | McGary et al. | |
| 5,064,419 A | 11/1991 | Gaarde | |
| 5,067,490 A | 11/1991 | Haber | |
| 5,067,945 A | 11/1991 | Ryan et al. | |
| 5,070,885 A | 12/1991 | Bonaldo | |
| 5,084,018 A | 1/1992 | Tsao | |
| 5,085,640 A | 2/1992 | Gibbs | |
| 5,086,780 A | 2/1992 | Schmitt | |
| 5,092,851 A | 3/1992 | Ragner | |
| 5,104,378 A | 4/1992 | Haber et al. | |
| 5,112,316 A | 5/1992 | Venturini | |
| 5,114,410 A | 5/1992 | Batlle | |
| 5,120,311 A | 6/1992 | Sagstetter et al. | |
| 5,125,414 A | 6/1992 | Dysarz | |
| 5,180,369 A | 1/1993 | Dysarz | |
| 5,180,370 A | 1/1993 | Gillespie | |
| 5,188,599 A | 2/1993 | Botich et al. | |
| 5,188,613 A | 2/1993 | Shaw | |
| 5,193,552 A | 3/1993 | Columbus et al. | |
| 5,201,710 A | 4/1993 | Caselli | |
| 5,211,628 A | 5/1993 | Marshall | |
| 5,211,629 A | 5/1993 | Pressly et al. | |
| 5,219,333 A | 6/1993 | Sagstretter et al. | |
| 5,259,392 A | 11/1993 | Schmitt | |
| 5,267,977 A | 12/1993 | Feeney, Jr. | |
| 5,292,314 A | 3/1994 | D'Alessio et al. | |
| 5,336,187 A | 8/1994 | Terry et al. | |
| 5,344,407 A | 9/1994 | Ryan | |
| 5,346,480 A | 9/1994 | Hess et al. | |
| 5,385,551 A | 1/1995 | Shaw | |
| 5,389,076 A | 2/1995 | Shaw | |
| 5,389,085 A | 2/1995 | D'Alessio et al. | |
| 5,395,337 A | 3/1995 | Clemens et al. | |
| 5,403,286 A | 4/1995 | Lockwood, Jr. | |
| 5,423,758 A | 6/1995 | Shaw | |
| 5,478,316 A | 12/1995 | Bitdinger et al. | |
| 5,480,385 A | 1/1996 | Thorne et al. | |
| 5,578,011 A | 11/1996 | Shaw | |
| 5,582,597 A | 12/1996 | Brimhall et al. | |
| 5,613,952 A | 3/1997 | Pressly, Sr. et al. | |
| 5,616,135 A | 4/1997 | Thorne et al. | |
| RE35,539 E | 6/1997 | Bonaldo | |
| 5,688,241 A | 11/1997 | Asbaghi | |
| 5,695,475 A | 12/1997 | Best, Jr. et al. | |
| 5,709,669 A | 1/1998 | Haining | |
| 5,769,826 A | 6/1998 | Johnson et al. | |
| 5,810,775 A | 9/1998 | Shaw | |
| 5,836,917 A | 11/1998 | Thorne et al. | |
| 6,024,710 A | 2/2000 | Miller | |
| 6,024,727 A | 2/2000 | Thorne et al. | |
| 6,186,980 B1 | 2/2001 | Brunel | |
| 6,190,361 B1 | 2/2001 | Gettig et al. | |
| 6,203,529 B1 | 3/2001 | Gabriel et al. | |
| 6,379,336 B1 | 4/2002 | Asbaghi et al. | |
| 6,623,458 B2 | 9/2003 | Woehr et al. | |
| 6,641,555 B1 | 11/2003 | Botich et al. | |
| 6,761,706 B2 | 7/2004 | Vaillancourt | |
| 6,860,871 B2 | 3/2005 | Kuracine et al. | |
| 6,869,415 B2 | 3/2005 | Asbaghi | |
| 7,357,783 B2 | 4/2008 | Millerd | |
| 2001/0044607 A1 | 11/2001 | DeMichele et al. | |
| 2005/0288607 A1 * | 12/2005 | Konrad | 600/576 |
| 2007/0149894 A1 * | 6/2007 | Heske et al. | 600/566 |

FOREIGN PATENT DOCUMENTS

| | | |
|---|---|---|
| JP | 2502076 | 7/1990 |
| JP | 3504209 | 9/1991 |
| JP | 7246196 | 9/1995 |
| WO | WO 95/08358 | 3/1995 |
| WO | WO 95/16389 | 6/1995 |
| WO | WO 96/05879 | 2/1996 |
| WO | WO 98/48869 | 11/1998 |
| WO | WO 98/52630 | 11/1998 |
| WO | WO0038566 | 7/2000 |
| WO | WO0049939 | 8/2000 |
| WO | WO2004030539 | 4/2004 |

OTHER PUBLICATIONS

"BD Vacutainer: Push Button Blood Collection Set" BD Diagnostics. *Manual* (13 pages).

* cited by examiner

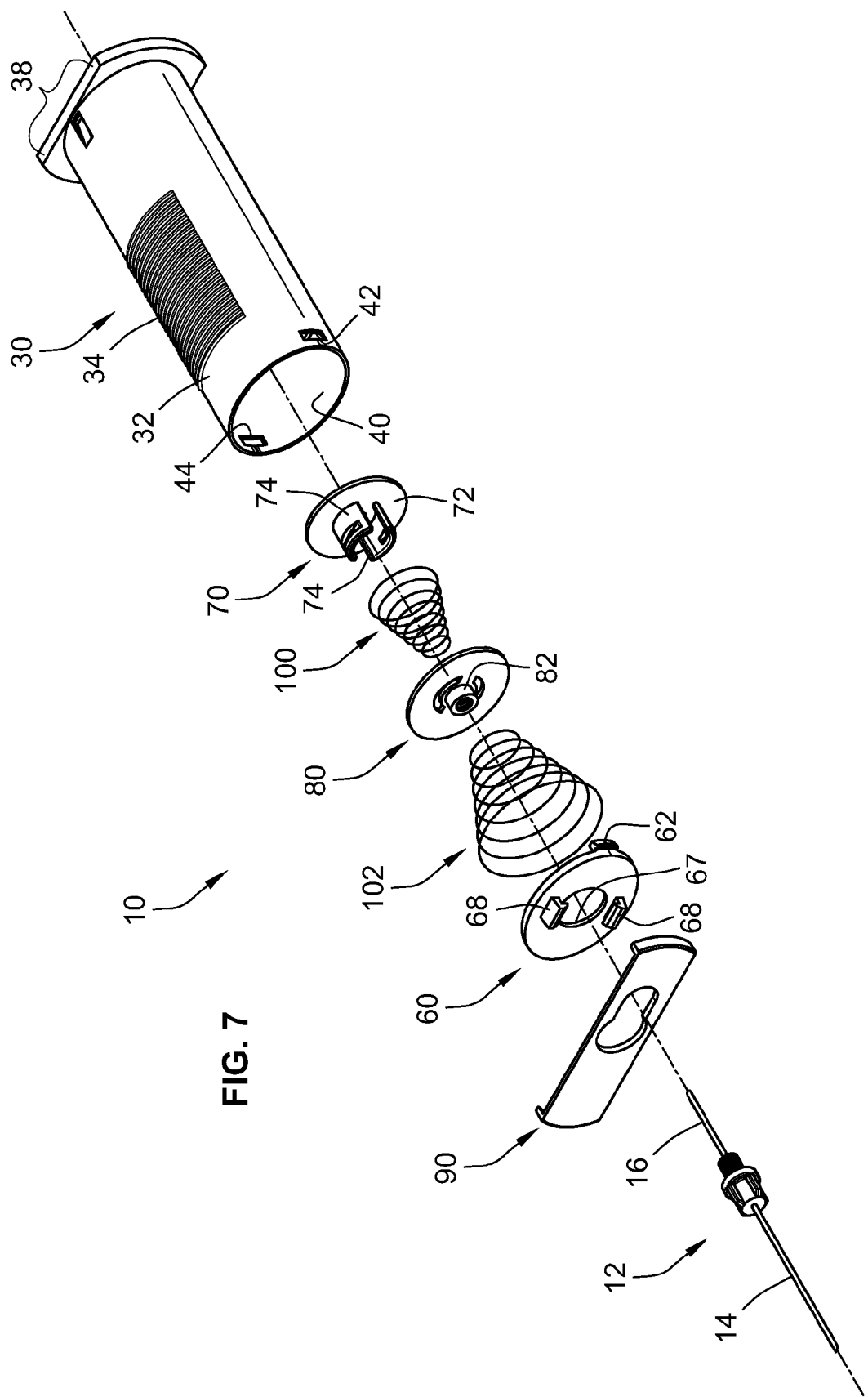

RETRACTABLE NEEDLE-SAFETY BLOOD SAMPLING DEVICE

CLAIM OF PRIORITY AND CROSS-REFERENCE TO RELATED APPLICATIONS

This application claims the benefit of and priority to U.S. Provisional Patent Application No. 61/162,096, filed on Mar. 20, 2009, the content of which is incorporated herein by reference in its entirety.

FIELD OF THE INVENTION

The present invention relates generally to hypodermic needles. In particular, the present invention relates to hypodermic needle devices, for collecting samples of blood or other body tissues, that conceal the sharp point(s) of the hypodermic needle following use.

BACKGROUND OF THE INVENTION

A hypodermic needle is a sharp, hollow needle intended to penetrate or puncture the skin, mucous membrane, and internal organs of humans or animals for insertion or removal of fluids, aerosols, or particulate suspensions. The hypodermic needle is commonly used with a syringe to inject substances into the body or extract fluids from the body. Such needles may also be used to take liquid samples from the body, e.g., for taking blood from a vein in venipuncture.

When a hypodermic needle enters a patient's body, it is invariably contaminated by the patient's blood, body fluids, etc. Following use of the syringe, the hypodermic needle presents a risk to the administering and assisting physicians, nurses, and other health care personnel because the needle might transmit an infection or disease to such personnel if it were to accidentally puncture them. Others susceptible to accidental needle punctures include sanitation workers who later dispose of garbage containing the hypodermic needles. Often, the accidental needle puncture may be so trivial that it remains unrecognized and, thus, untreated until more serious side effects become apparent.

Both healthy and sick people are subject to diagnostic blood drawing, while only sick patients typically receive therapeutic injections. Since there are more healthy people than sick ones, the incidence of accidental needle stick injuries and microbial disease transmission caused by blood drawing devices far exceeds that caused by syringes used for therapeutic injections given to sick persons. In addition, because the needles used for drawing blood have sharp puncturing points on both ends, in contrast to therapeutic syringe needles with a single sharp end, the chance for needle stick injury is normally higher with blood drawing devices.

Automatic retraction of post-use sharp points by hypodermic syringe assemblies with safety engineered devices is an effective way to guard against accidental needle sticks and inadvertent microbial transmission. Heretofore, simple, inexpensive and effective retraction mechanisms have not been made available or adaptable for blood drawing devices. This is especially so because the double-ended needle poses special problems. For instance, when such retraction devices are applied to dual-point hypodermic needles, retraction of the distal sharp end often results in projection and injury potential of the proximal sharp end. Further, the needle may be screwed to the end of the barrel, which makes retraction of the needle difficult or impossible.

The Design Criteria

Improved engineering controls are often among the most effective approaches to reducing occupational hazards, and therefore are an important element of a needle stick prevention program. Such controls include eliminating the unnecessary use of needles, and implementing devices with safety features. A number of sources have identified the desirable characteristics of safety devices [OSHA 1999c; FDA 1992; Jagger et al. 1988; Chiarello 1995; Quebbeman and Short 1995; Pugliese 1998; Fisher 1999; ECRI 1999]. These characteristics include the following:

The device is needleless.
The safety feature is an integral part of the device.
The device preferably works passively (i.e., it requires no activation by the user). If user activation is necessary, the safety feature can be engaged with a single-handed technique and allows the worker's hands to remain behind the exposed sharp.
The user can easily tell whether the safety feature is activated.
The safety feature cannot be deactivated and remains protective through disposal.
The device performs reliably.
The device is easy to use and practical.
The device is safe and effective for patient care.

Although each of these characteristics is desirable, some are not feasible, applicable, or available for certain health care situations. For example, needles will always be necessary where alternatives for skin penetration are not available. Also, a safety feature that requires activation by the user might be preferable to one that is passive in some cases. Each device must be considered on its own merit and ultimately on its ability to reduce workplace injuries. The desirable characteristics listed here should thus serve only as a guideline for device design and selection.

In light of the foregoing, significant inventive efforts have been devoted to concealing the sharp point(s) of hypodermic needles. One such effort is described in U.S. Pat. No. 5,338,311, entitled "Hypodermic Needle Assembly," which issued to the inventor of the present invention on Aug. 16, 1994. A needle-syringe assembly is presented with a needle holder carrying the hypodermic needle on a distal end thereof. The needle holder is slidably mounted in a coaxial cavity of the plunger. To retract the needle, a taper lock is disengaged by rotary movement of the plunger relative to the barrel. While preventing rotation of the needle holder relative to the barrel, continued rotation of the plunger causes a lateral arm of the needle holder to ascend through a helical slot in the plunger so that the needle holder retracts into the coaxial cavity of the plunger and the needle is concealed inside the barrel. A similar device is disclosed in U.S. Pat. No. 5,514,100, entitled "Hypodermic Needle Assembly," which issued to the inventor of the present invention on May 7, 1996.

Other devices include the Punctur-Guard™ device, manufactured by Bio-Plexus, Inc., of Ventura, Calif., USA. In this device, a coaxial tube is inserted inside the post-use hypodermic needle, projecting beyond the sharp point. This avoids the puncture of the skin by sharp bevel, but does not prevent scratching and microbial transmission.

A cap activated device is disclosed in U.S. Pat. No. 5,810,775 (RE 39107), to Shaw, which is entitled "Cap Operated Retractable Medical Device." In Shaw, a spring is installed in a compressed state under a needle carrier by a tapered co-axial sleeve inside an adapter. When the cover of the adapter is closed, an inner co-axial tube is pushed down to release the needle carrier, allowing the spring to expand and retract the needle carrier into the adapter tube. The Shaw device has many disadvantages. First, the needle is free and likely to fall off when the cap is opened. In addition, the opening at the bottom of the adapter tube remains open, and there is a potential for aerosolization of contaminated blood upon retraction.

Other attempts have been made to resolve the needle stick problem, but a satisfactory solution is still not available. By way of example, in U.S. Pat. No. 5,070,885, to Bonaldo, which is entitled "Disposable Blood Collection Device", a movable carrier for the double-ended needle is installed within an adapter. The carrier is accessible from outside the adapter via a manual switch that extends through a longitudinal slot on the adapter. The manual switch allows an operator to force the needle carrier proximally, permitting retraction of the needle. Similarly, U.S. Pat. Nos. 4,813,426, to Haber et al., and 4,892,107, to Haber, also install a needle carrier sleeve that is accessible and controlled through a longitudinal slot on the adapter wall, and is controlled manually or by a spring.

U.S. Pat. No. 4,904,242, to Kulli, provides an internal anchor for a double-ended needle, and retracts the needle with an extension spring. U.S. Pat. No. 4,984,580, to Wanamaker, provides a concentric chamber in the nozzle area of the adapter to accommodate the hub of a double-ended needle. Wanamaker's hub is encircled by a compression spring. A spring release mechanism, which is accessed by a window close to the nozzle, retracts the needle when actuated.

A needle device and method of use are described in U.S. Pat. No. 5,193,552, to Columbus, wherein the needle moves out of and into a protective housing, between two operative positions, one of which causes the housing to shield the needle. Each operative position includes releasable locking detents that operate to temporarily hold the needle in one of the positions, the holding force of one detent being less than that of the other. A third position beyond the one that shields the needle in the housing is used to permanently lock the needle in the housing against accidental reuse. The needle device can be used with a blood collection container or a syringe drug delivery container, each one releasably mating with the device during use.

U.S. Pat. No. 6,869,415 B2, to Asbaghi, provides a protective guard that automatically covers the needle after a blood collection procedure has been completed. Prior to the procedure the guard member is restrained on the device in a proximal position to expose the needle, and to thereby facilitate insertion of the needle into a vein of a patient. When a blood collection vial is engaged with the device, the guard member is released to move distally over the needle. As the needle is being withdrawn from the patient, the guard member automatically covers the needle.

U.S. Pat. No. 7,357,783 B2, to Millerd, also describes a blood collection device wherein the entire double-ended needle is pulled into and covered by an adapter. Initially, the needle assembly is advanced and the vein-puncturing needle is exposed to collect blood. Another needle guard remains anchored to the proximal sample-collecting end of the double-ended needle. When a collection tube is forced on the inner sample-collecting end, the latch is released and advances to cover the vein-puncturing needle. At the end of the procedure the sample-collecting sharp end is still bare to cause contaminated needle stick.

U.S. Pat. Nos. 5,346,480, to Hess et al., 5,292,314, to D'Allessio et al., 5,049,136, to Johnson, 4,923,447, to Morgan, and 4,170,993, to Alvarez, are other examples of needle cover devices. Most currently used devices simply cover the external venipuncture tube by a hinged sheath or retracting needle, while leaving the tube-puncturing sharp point exposed and unsafe. In addition, most of the currently available devices are expensive, and are not inherently safe. Many still have the potential of causing accidental needle punctures and microbial transmission. Most must be disposed of in sharps containers, which increases cost, and sharps containers are not available or affordable to ¾ of the world population.

SUMMARY OF THE INVENTION

One object of the present invention is to provide an inexpensive, easy-to-use, fully-integrated, and precision-engineered safety adapter device for a blood-drawing double-ended hypodermic needle.

Another object of this invention is to provide an engineered safety blood-drawer adapter device that, upon completion of collection of samples and upon voluntary actuation by a user, retracts the double sharp-ended hypodermic needle, and secures it in a totally enclosed, individual, tamper-proof container.

An additional object of this invention is to conveniently locate the actuation point with respect to the grip surface of the blood-drawer, and locate the actuation point well behind the needle body.

One more object of the present invention is to utilize a conventional double-ended hypodermic needle whose one puncturing end enters into a vein, while the opposing end punctures the rubber stopper to transmit the sample into a vacuumed tube. The size, shape, and structure of the blood drawer needle, as well as its operation, are conventional in many respects, except that the adapter is uniquely designed to accept and conceal the entire length of the double-ended needle.

An additional object is to permit healthcare personnel to use the same blood sampling method, the same double-ended needle, and the same sample tube they have been comfortably using for years, but may be prohibited from using in their present state due to changes in the law and safety concerns. The objective is to resolve the safety concerns so that the same inexpensive method of blood sampling and convenience is available again. Accordingly, the safety device of the present invention, although structurally different and unique, may be used in exactly the same way as other conventional devices which have been used for years, eliminating the need for special training on the part of the user.

It is another object of this invention that the adapter tube engaging the double ended needle be engineered and lengthened to retract both sharp ends of the double ended needle inside the lengthened body of the adapter, and completely conceal the needle by closing both ends of the adapter tube. This design adds internal safety features to make it safe.

It is yet another object of this invention that the safety mechanism be tamper proof, and the device be inherently safe, meaning that it has no potential of post use puncturing of skin and logically no need of requiring disposal in a sharps container for the second time.

Another object of this invention is to present an adapter that is itself an automatic safe and tamper proof container configured to retract and securely lock a double-ended sharp hypodermic needle after use, and securely close both ends of the adapter on a simple push of an actuator plate, eliminating any potential to cause needle stick injuries after use.

Another object of this invention is to provide a safety device wherein the primary functional components are inseparable from the device assembly. Otherwise, in the event of real necessity, the functionality of the device may not be available.

According to one embodiment of the present invention, the safety adapter includes four plastic disks or plates—a top plate, a needle holder plate, an actuator plate, and a bottom plate, along with two specialty springs. This permits the device to be made at relatively modest cost, which is a major concern for the healthcare industry.

In accordance with another embodiment, the retraction mechanism is actuated at the back end of the puncturing needle by a lateral touch on a locking plate, as required by NIOSH and OSHA. In this instance, the safety device instantly retracts the hypodermic needle, and closes the opening. The dangerous double-ended sharp needle is totally and permanently enclosed in a rigid, puncture resistant, lengthened, plastic adapter tube, with both ends of the tube mechanically closed.

As part of yet another facet of the disclosed concepts, the needle, when in a retracted state, is held in a concentric orientation with respect to the central axis of the adapter tube, with neither of the sharp points making contact with the sides or end enclosures of the tube.

According to another aspect of this invention, the mechanical closure of the distal end prevents reactive aerosolization prevalent in other retractable needle devices. The short end of the needle does not generate aerosolization because the intraluminal inertia of the fluid is in the opposite direction. A square opening in the proximal plate has a generally square shape that allows, for example, rotation of the plate for engagement and alignment with other components.

The above features and advantages, and other features and advantages of the present invention, will be readily apparent from the following detailed description of the preferred embodiments and best modes for carrying out the present invention when taken in connection with the accompanying drawings and appended claims.

BRIEF DESCRIPTION OF THE DRAWINGS

FIG. 7 is an exploded, perspective-view illustration of a hypodermic needle safety device in accordance with the present invention;

Figure 1:
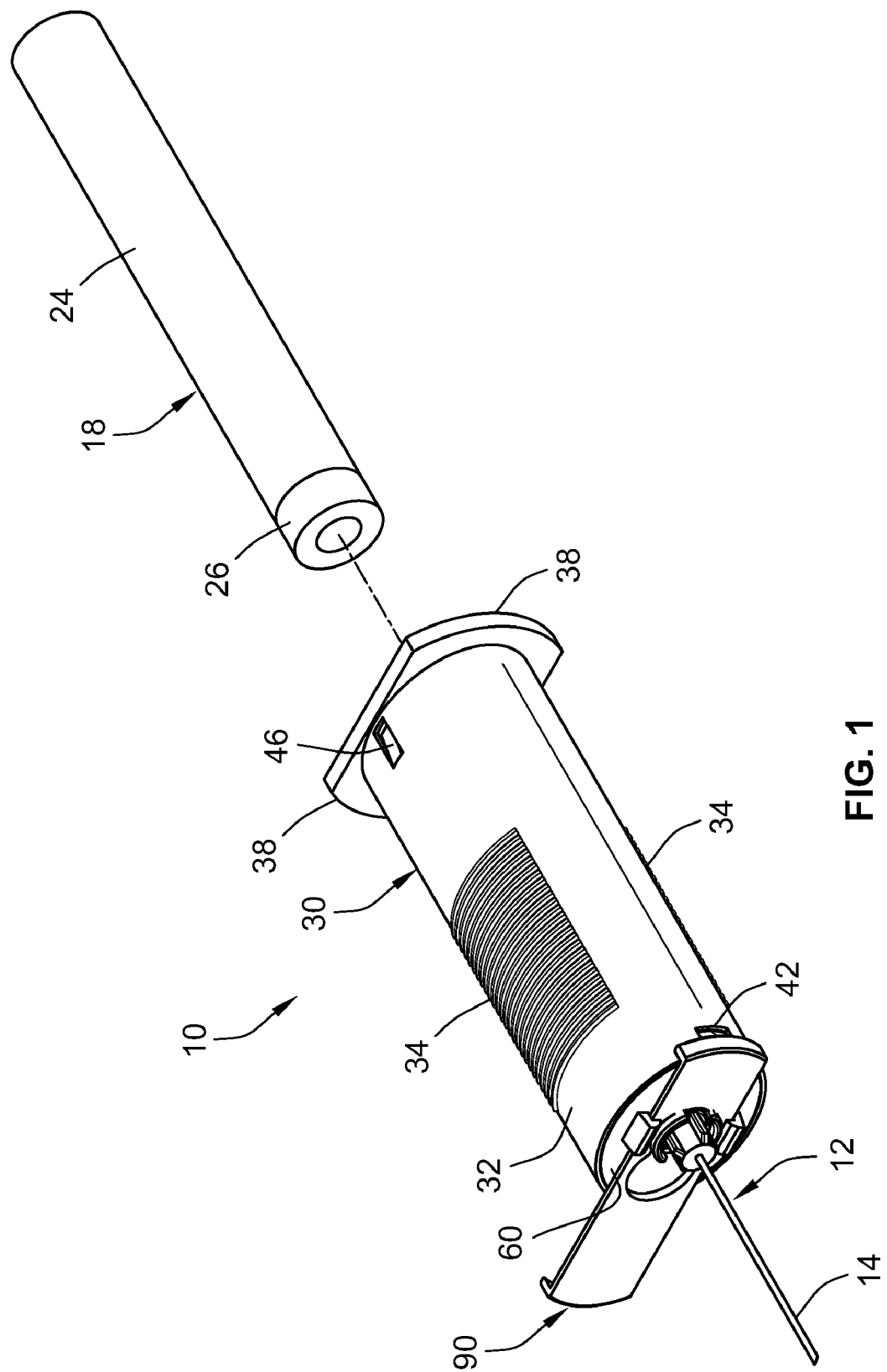
FIG. 1 is a perspective-view illustration of a hypodermic needle safety device in accordance the present invention, showing the sample-intake end of a double-ended hypodermic needle in an extended position, and a vacuum tube for collection of fluid samples positioned for mating with an opposing sample-output end of the hypodermic needle.

While the invention is susceptible to various modifications and alternative forms, specific embodiments thereof have been shown by way of example in the drawings and will be described in detail herein. It should be understood, however, that the invention is not intended to be limited to the particular forms disclosed. On the contrary, the invention is to cover all modifications, equivalents, and alternatives falling within the spirit and scope of the invention as defined by the appended claims.

DETAILED DESCRIPTION OF ILLUSTRATED EMBODIMENTS

While this invention is susceptible of embodiments in many different forms, there are shown in the drawings and described herein in detail preferred embodiments of the invention with the understanding that the present disclosure is to be considered as an exemplification of the principles of the invention, and is therefore not intended to limit the broad concepts of the invention to the embodiments illustrated.

Referring to the drawings, wherein like reference numbers refer to like components throughout the several views, presented in FIG. 1 is a perspective-view illustration of a hypodermic needle safety device at 10. The safety device 10 is shown with a first, distal end 14 (e.g., "sample-intake end") of a double-ended hypodermic needle 12 protruding from an opening in a distal end of a needle holder 30 (also referred to herein as "adapter"). A fluid-sample collection device, represented herein as vacuum tube 18, is operable to receive and collect fluids through the double-ended hypodermic needle 12. The vacuum tube 18 is shown in FIG. 1 positioned for operative mating with a second, proximal end 16 (e.g., "sample-output end" shown, for example, in FIG. 2) of the hypodermic needle 12. The double-ended hypodermic needle 12 and vacuum tube 18 are optional components, which may be provided separately from the safety device 10, or included as a single assembly with the safety device 10. Also, the geometry, dimensions, and general configuration of the hypodermic needle 12 and vacuum tube 18 may be individually or collectively modified to meet the particular design requirements of the intended application of the safety device 10.

Figure 2:
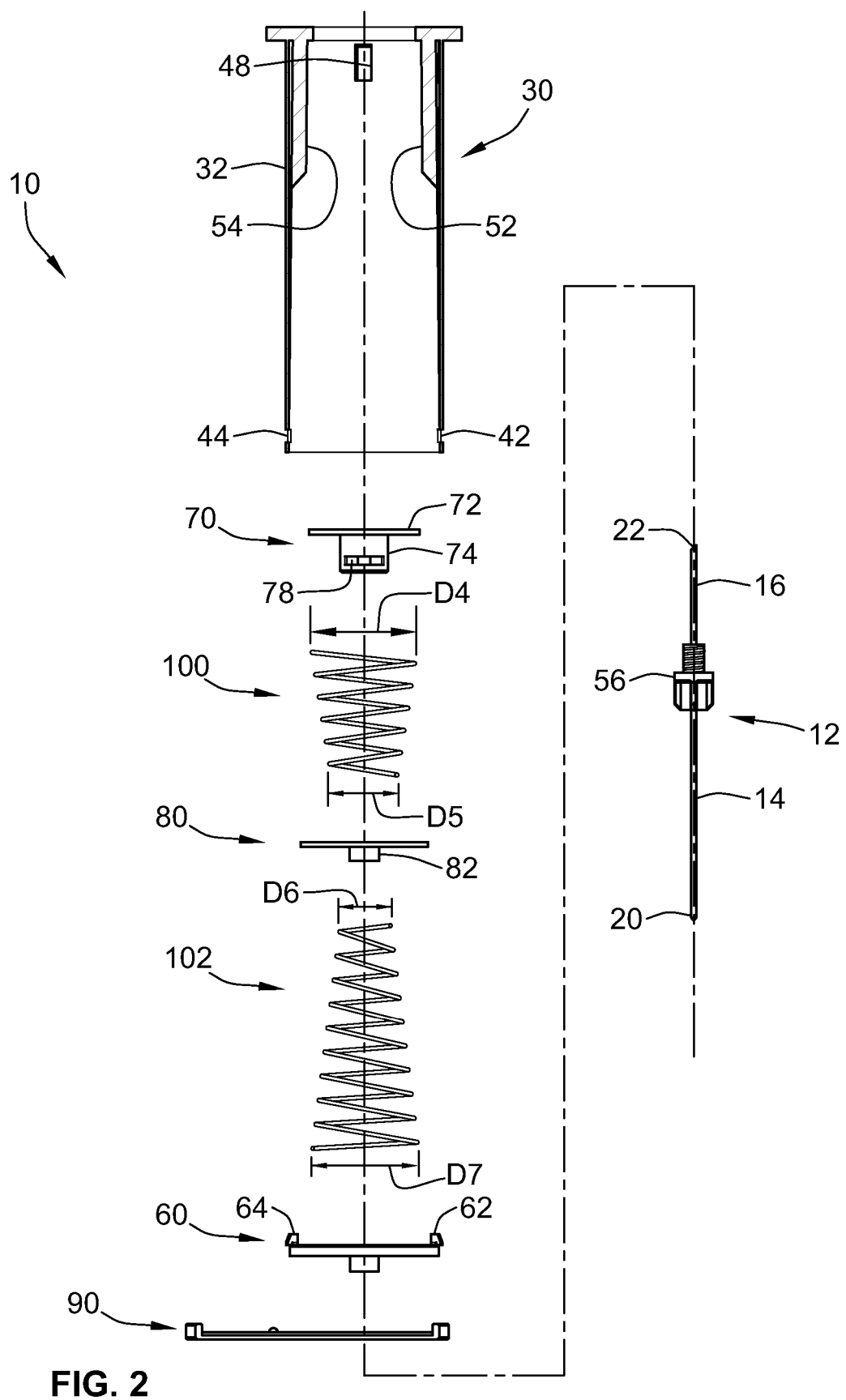
FIG. 2 is an exploded, plan-view illustration in partial cross-section of a hypodermic needle safety device in accordance with the present invention.

In the illustrated embodiment, each of the two needle ends 14, 16 has a sharp/sharpened tip, respectively designated as 20 and 22 in FIG. 2. In certain applications of the present invention, the first sharp tip 20 of the hypodermic needle 12 may be considered a "puncturing end," designed to pierce/penetrate human or animal skin, organs, veins, etc. The second sharp tip 22 may be considered a "distributing end," designed to distribute fluid samples received by the sample-intake end 14 of the hypodermic needle 12. By way of example, the fluid-sample collection device 18 of FIG. 1 includes a generally cylindrical body 24 with a rubber stopper 26 mounted to a distal end of the cylindrical body 24, providing a fluid-tight, vacuum seal. In this instance, the sample-output end 16 of the hypodermic needle 12 is operable to press into and puncture the rubber stopper 22 so that the vacuum in the tube 18 draws a fluid sample through the needle 12 into the tube 18.

With continued reference to FIG. 1, the needle holder 30 comprises an elongated tubular body 32, which may have a generally oval-shaped longitudinal cross-section (as shown) or other design (e.g., a circular or elliptical perimeter). The needle holder 30 is provided with optional raised, serrated external surfaces 34 on opposing portions of the holder body 32. The serrated surfaces 34 provide an operator with a high-friction, non-slip grip during use of the safety device 10. The needle holder body 32 may be fabricated as a single, unitary part, or molded in separate parts that are thereafter assembled. Likewise, the serrated surfaces 34 may be preformed into the needle holder body 32, or provided as a separate add-on feature that is adhered or otherwise attached to the holder body 32.

Figure 5:
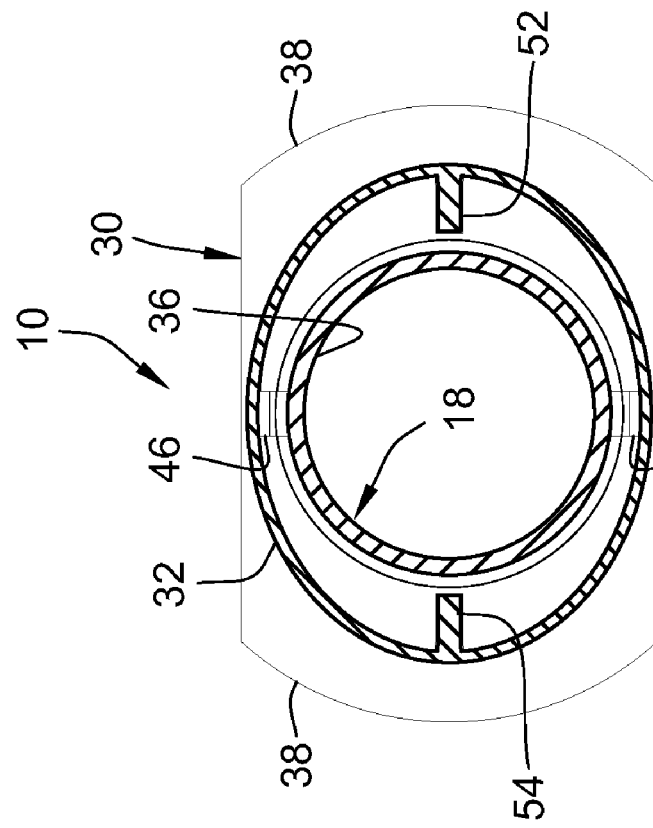
FIG. 5 is a front-view illustration of the hypodermic needle safety device of FIG. 3, taken in partial cross-section along line B-B.
Figure 9:
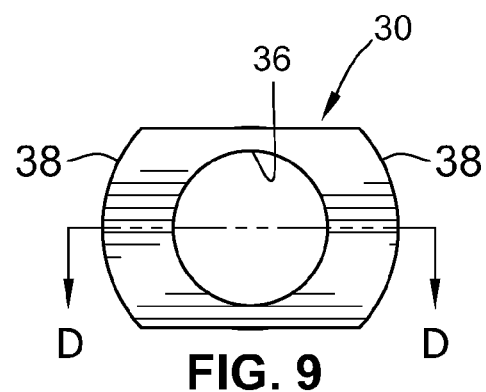
FIG. 9 is a rear-view illustration of the needle holder of FIG. 8.

As seen in FIGS. 5 and 9, the needle holder body 32 has at its proximal end a circular opening 36 to provide access for the sample-collection (vacuum) tube 18. In addition, the proximal end of the needle holder 30 has a pair of identical tabs or flanges 38 that protrude laterally outward from opposite sides of the holder body 32. These tabs 38 provide counter balancing leverage and control for pushing the vacuum tube 18 into the needle holder 30, for collection of a sample, and for withdrawing the tube 18 after obtaining the fluid sample. This process may be repeated to obtain multiple samples for different tests.

Figure 4:
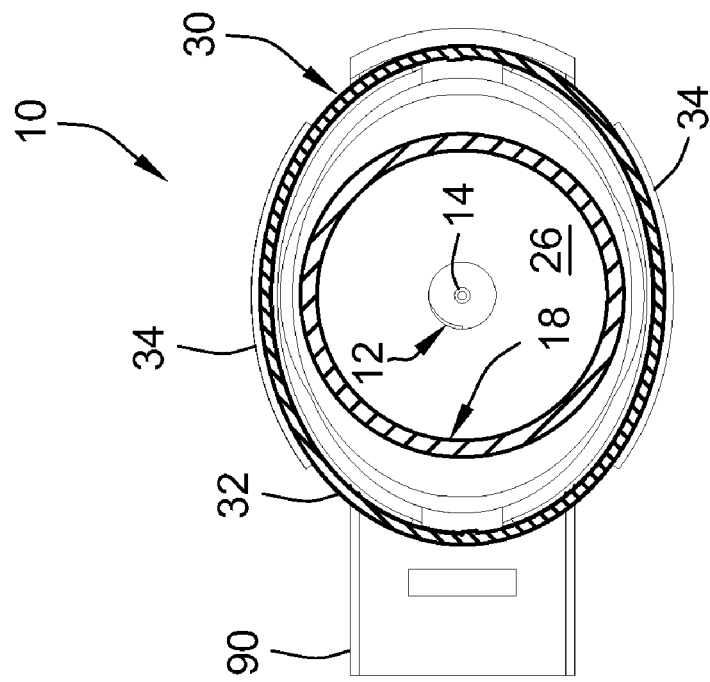
FIG. 4 is a rear-view illustration of the hypodermic needle safety device of FIG. 3, taken in partial cross-section along line A-A.
Figure 10:
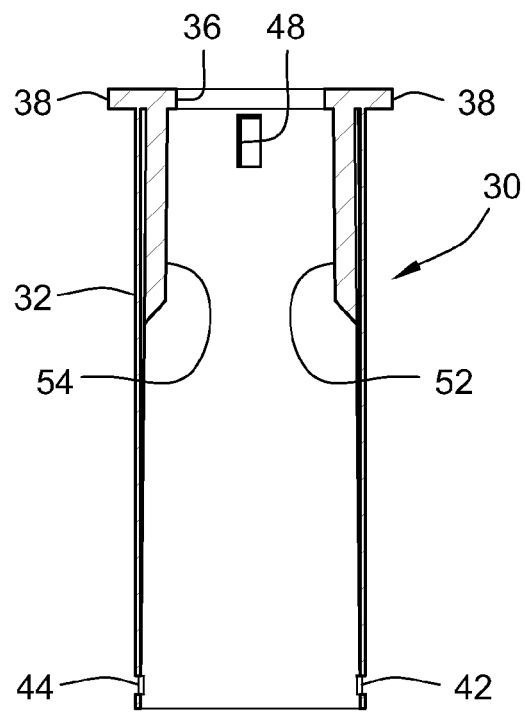
FIG. 10 is a side-view illustration of the needle holder of FIG. 8, taken in partial cross-section along line D-D of FIG. 9.
Figure 11:
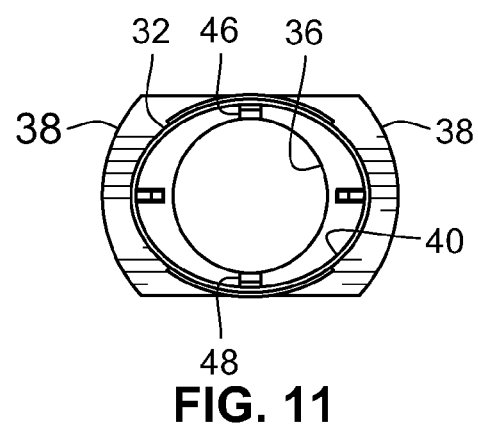
FIG. 11 is a front-view illustration of the needle holder of FIG. 8.

In the illustrated embodiment, the distal end of the adapter tube 30 has a generally oval-shaped opening 40, which is most clearly visible in FIGS. 4, 7 and 11. The holder body 32 is provided with a plurality of side windows, such as first and second side windows 42 and 44, respectively, shown in FIGS. 2, 7 and 10. In the illustrated embodiment, the windows 42, 44 are formed through sidewalls of the holder body 32, laterally offset from one another on opposing sides of the adapter tube 30 proximal to the distal opening 40. Each side window 42, 44 is configured to receive and engage with a respective projection 62, 64 of a bottom plate 60 (seen in FIG. 2). When both projections 62, 64 are operatively mated with a corresponding window 42, 44, the bottom plate 60 is locked to the adapter tube body 32, and operates to partially close off or otherwise obstruct the oval-shaped opening 40 of the adapter tube 30.

Figure 8:
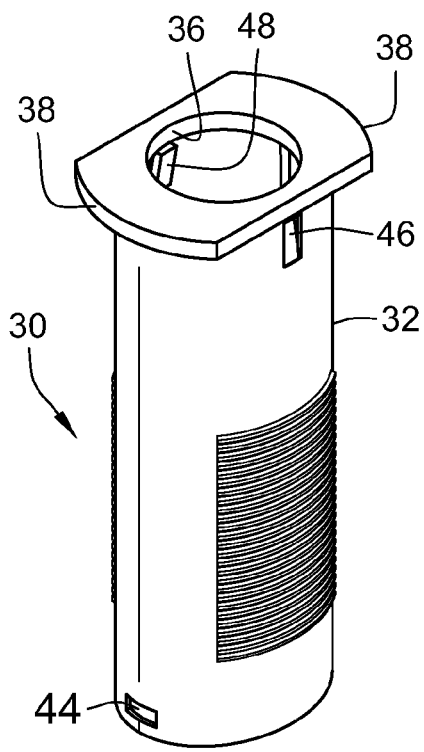
FIG. 8 is a perspective-view illustration of an exemplary needle holder or adapter in accordance with the present invention.
Figure 30:
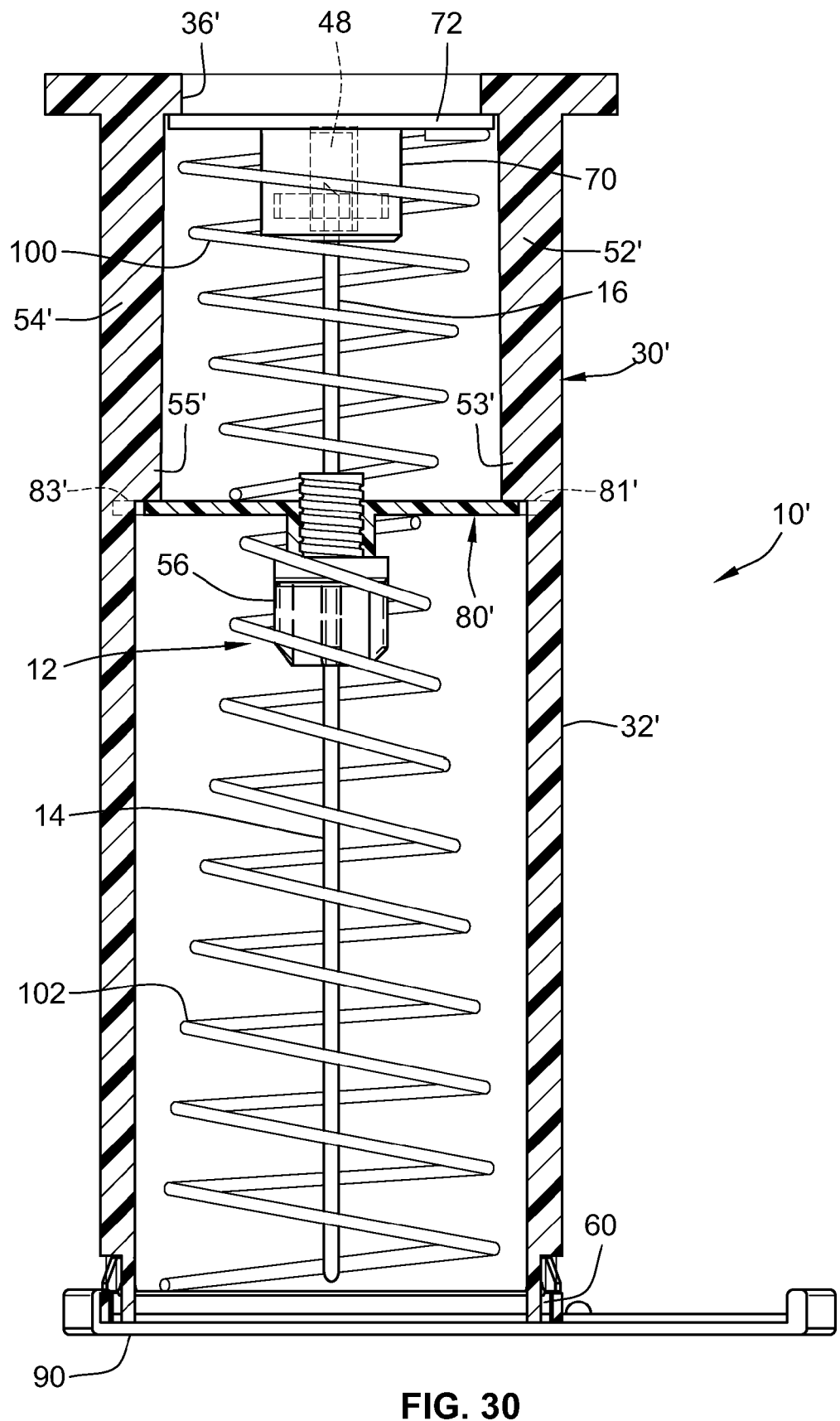
FIG. 30 is a plan-view illustration of an exemplary hypodermic needle safety device in accordance with an alternate embodiment of the present invention, with an outer protective adapter broken away in partial cross-section to show a double-ended hypodermic needle encased in the adapter, with total irreversible closure of both ends of the adapter.

Adjacent the proximal end of the needle holder 30 are two cavities with detents 46 and 48 (FIGS. 5, 8 and 11). In the illustrated embodiment, the detents 46, 48 project inwardly from opposing sides of the adapter tube body 32. These flexible detents 46, 48 may be molded into the tubular body 32 with an internal memory bend. By way of example, and not limitation, the detents 46, 48 are designed to selectively lock a top plate 70 (also referred to herein as "hub") to the proximal end of the tubular body 32 to thereby substantially close off or otherwise obstruct the circular opening 36. When the top plate 70 is forced rearwardly with respect to the adapter 30 toward the proximal opening 36, as will be described in more detail below, the outer perimeter of the hub base 72 engages forward-facing ramp surfaces 45 and 47 (FIG. 6) of the detents 46, 48, respectively. In so doing, the detents 46, 48 are deflected outwardly so that the top plate 70 can pass from one side to the other. The detents 46, 48 then flex back inwardly to lock the top plate 70 in place, pinning the top plate 70 between the detents 46, 48 and the inner surface of the adapter tabs 38, securely closing the circular opening 36, as seen in FIG. 30.

Figure 6:
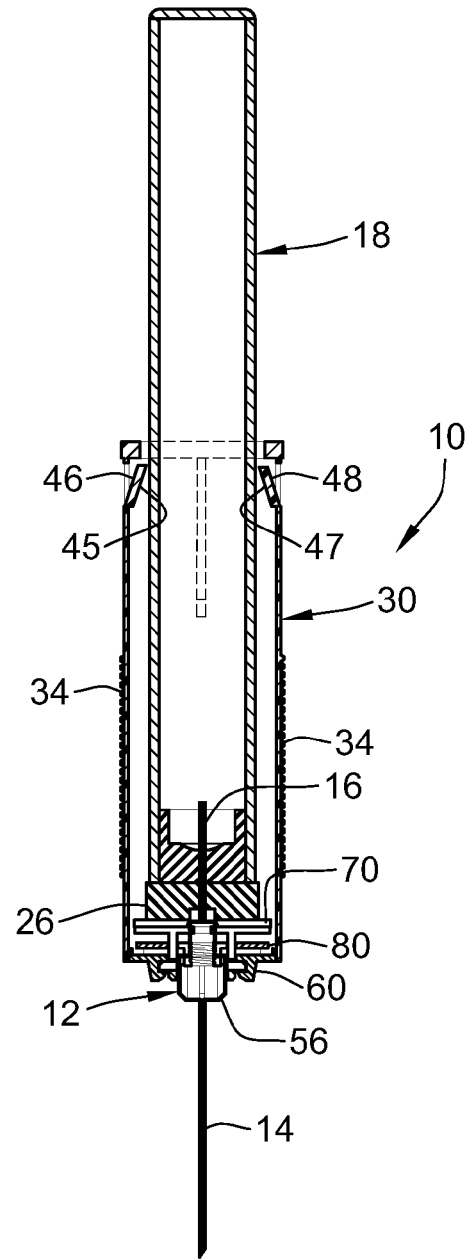
FIG. 6 is a side-view illustration of the hypodermic needle safety device of FIG. 3, taken in partial cross-section along line C-C.

According to the exemplary embodiment shown, the overall width W1 of the holder body 32, seen in FIG. 4, is larger than the height H1, seen in FIG. 6. While the external dimensions of the adapter 30 are preferably uniform along the length of the tubular body 32, the internal dimensions are intentionally made non-uniform. For instance, in the illustrated embodiment, the distal portion of the holder body 32 has a first longitudinal cross-section, whereas the proximal portion of the holder body 32 has a second longitudinal cross-section. By way of example, with comparative reference to FIGS. 4 and 5, the interior of the distal portion has a generally oval-shaped cross-section (e.g., along line A-A), while the interior proximal segment of the holder body 32 is made generally circular by two diametral internal ribs 52 and 54 (e.g., along line B-B). The internal geometry of the adapter 30 provides a positive arrest point used to limit the speed and distance of retraction of the needle holder plate 70. In other words, the non-uniform, internal configuration of the tubular body 32 is designed to control the movement of selected constituents of the safety device 10, restricting certain retraction elements at desired positions along the length of the tubular body 32, as will be explained in detail below. Notably, the length, width, number, and orientation of the diametral ribs may be varied without departing from the scope of the present invention.

In some embodiments, the short diameter surface of the tubular body 32, proximal to the distal end thereof, provides an ergometrically smaller angle between the distal end 14 of the hypodermic needle 12 and the object to be penetrated (e.g., a patient's vein). By way of clarification, the central axis of the needle puncturing end 14 and a vein are preferably at a minimum possible angle to avoid inadvertent double puncture of vein walls. Such double puncture may result in bleeding under the skin and hematoma, which may be further exacerbated by the tourniquet applied to the arm to raise venous pressure. In addition, this segment of the adapter body 32 maintains a flat surface between the safety device 10 and the vein underneath. This is also a beneficial position for obtaining multiple samples with minimum movement of the needle 12.

In certain applications of the present invention, predetermined segments of the adapter 30, preferably along the short-diameter outer surface of the holder body 32, include friction lines to provide a secure hold for insertion of the puncturing end 20 of the needle 12, for example, into a vein or body cavity. As previously noted, the distal portion of the adapter 30 includes raised, serrated surfaces 34 that extend in an arcuate fashion along the outer surface the holder body 32 between major axis antipodal points of the oval-shaped cross-section. The serrated surfaces 34 increase sliding friction between the tubular body 34 and an object abutting therewith, thereby improving control of the entire syringe assembly.

Figure 16:
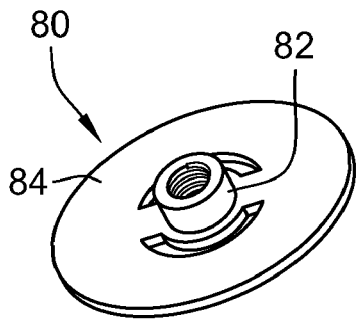
FIG. 16 is a perspective-view illustration of an exemplary needle holder plate in accordance with the present invention.
Figure 17:
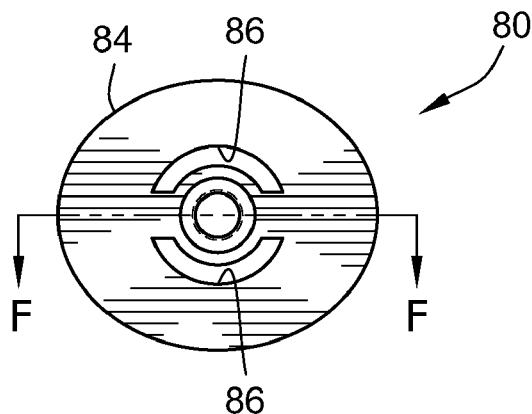
FIG. 17 is a front-view illustration of the needle holder plate of FIG. 16.
Figure 18:
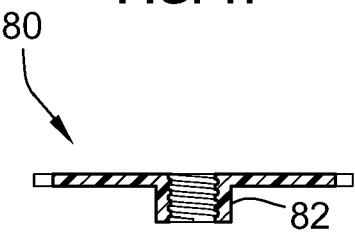
FIG. 18 is a side-view illustration of the needle holder plate of FIG. 16, taken in partial cross-section along line F-F of FIG. 17.
Figure 25:
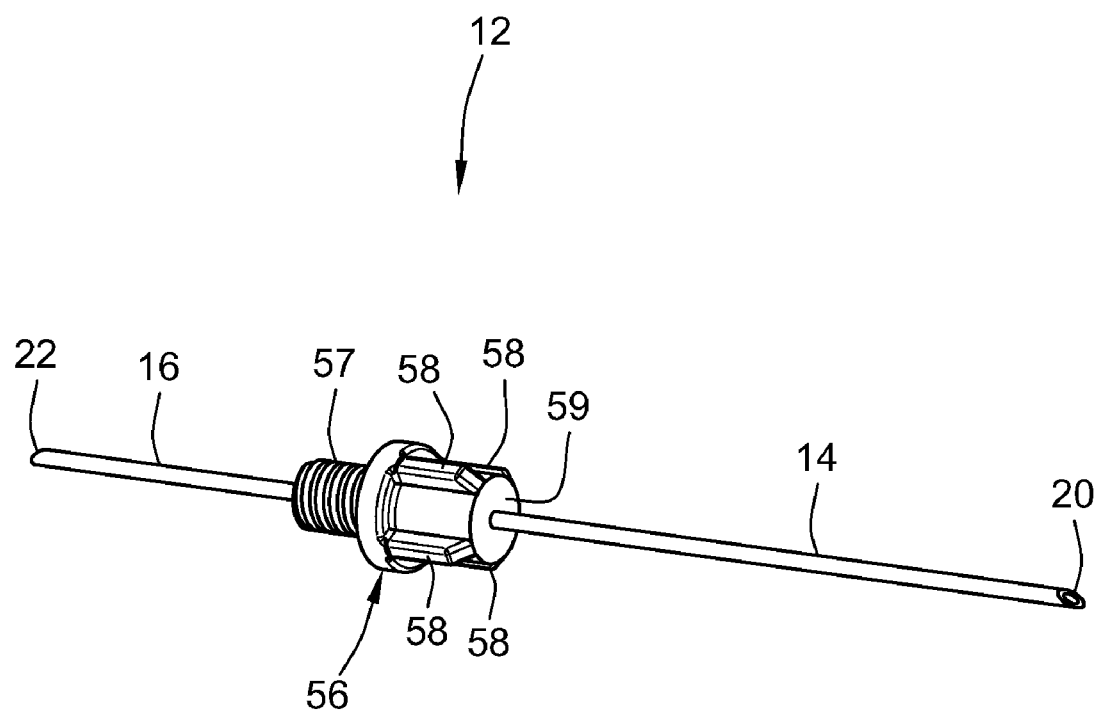
FIG. 25 is a perspective-view illustration of an exemplary double-ended hypodermic needle in accordance with the present invention.

Turning briefly to FIG. 25, the safety device 10 is used with a double-ended hypodermic needle 12. It is desirable that the two ends 14, 16 of the needle 12 be formed as a single, unitary body with opposing beveled edges, and a longitudinally-elongated internal channel (not specifically called out with reference numbers, but readily apparent in FIG. 25) that spans between, and fluidly connects respective openings in the puncturing end 20 and the distributing end 22. According to the illustrated representation, a connector 56 is operatively attached to the hypodermic needle 12 in between the distal and proximal ends 14, 16. The connector 56 may be insert molded to an intermediate section of the hypodermic needle 12 to provide a stable, operative anchoring for the needle 12. For instance, the illustrated connector 56 has an externally-threaded male luer hub 57 that operatively mates with (i.e., screws into) an internally threaded female luer hub 82 of a needle holder plate 80, best seen in FIGS. 16 and 18.

The connector 56 also has a plurality of raised ridges 58 configured to engage with a needle cover (not shown). In the embodiment illustrated in FIG. 25, four ridges 58 project radially outward from a central hub portion 59. The ridges 58 are designed to press-fit into the needle cover, securing the cover to the connector 56. In addition, the ridges 58 preferably engage with the needle cover such that the hypodermic needle 12 may be screwed to the needle holder plate 80 simply by pressing the male luer hub 57 into the female luer hub 82, and rotating the needle cover without exposing either of the sharp tips 20, 22. The double-ended needle may be fabricated in multiple sizes. Any dimensional disparity may be easily corrected by changing the length of the double-ended canola and altering the connector location.

Figure 20:
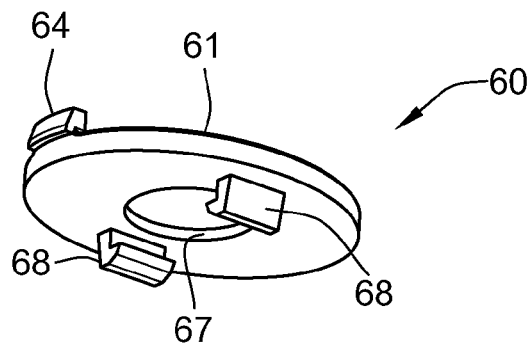
FIG. 20 is a perspective-view illustration of an exemplary bottom plate in accordance with the present invention.
Figure 22:
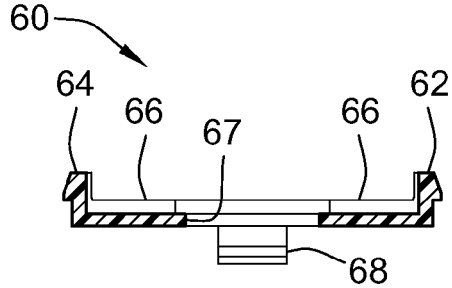
FIG. 22 is a side-view illustration of the bottom plate of FIG. 20, taken in partial cross-section along line G-G of FIG. 21.
Figure 21:
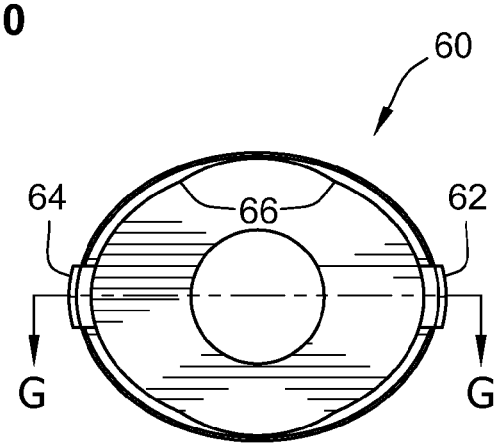
FIG. 21 is a rear-view illustration of the bottom plate of FIG. 20.

The bottom or distal end of the tube 32 of the adapter 30 is substantially closed off by a bottom plate 60, which is independently depicted in various views in FIGS. 20-22. The bottom plate 60 has a generally oval-shaped base 61. In preferred practice, the outer periphery of the base 61 matches the internal shape and dimensions of the distal portion of the holder tube body 32. The matching geometry permits a complementary fit and obligatory alignment of the bottom plate 60, as well as proper alignment and engagement of the triangular projections 62, 64 with the windows 42, 44 at the margins of the holder body 32. The bottom plate 60 may also be fabricated with elevated margins 66 (FIGS. 21 and 22) that extend along the outer perimeter of the base 61. These margins 66 are shown in FIG. 22 with chamfers to enter the distal portion of the holder body 32.

In some of the disclosed embodiments, the triangular projections 62, 64 are configured as snap fasteners, each having a flexible stem with a generally triangular head (neither of which is explicitly called out, but both are readily apparent in FIG. 22). When the bottom plate 60 is pressed coaxially into the oval-shaped opening 40 of the tubular body 32, the triangular projections 62, 64 flex inward until the head of each projection is properly aligned with a respective window 42, 44, at which point the projections 62, 64 straighten, fitting the head into the window. Once properly engaged with the windows 42, 44, the head of each projection lies within the inner perimeter of the window margins, and the stem extends along the inside of the tubular body 32. When the projections 62, 64 are fully engaged, it is practically impossible to separate the bottom plate 60 from the adapter 30 without breaking the tube 32 or otherwise intentionally disengaging one part from the other. Optionally, for additional safety, the mating margins may be bonded by solvents or via ultrasonic welding.

Figure 12:
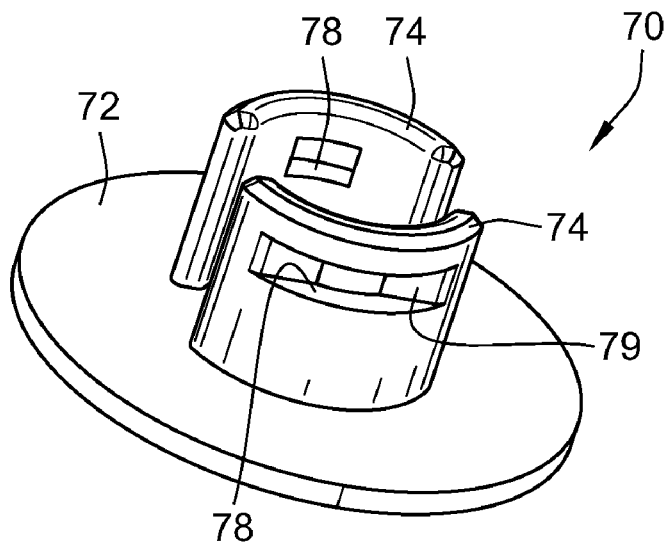
FIG. 12 is a perspective-view illustration of an exemplary top plate in accordance with the present invention.
Figure 13:
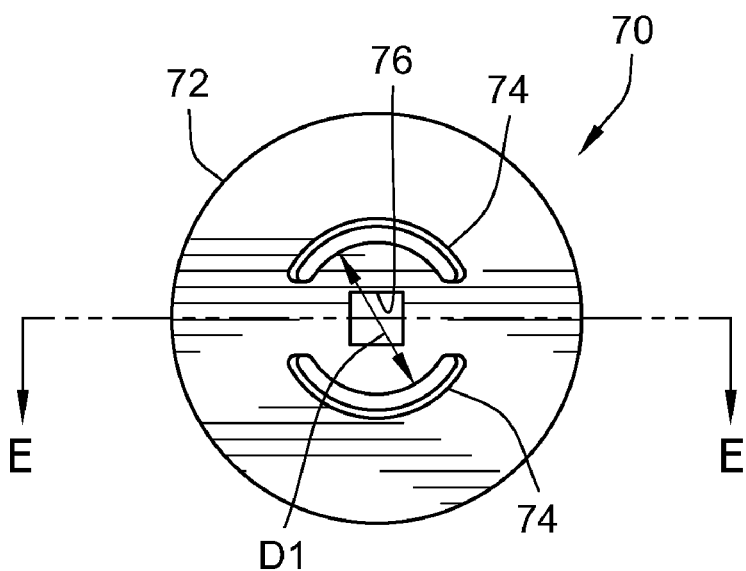
FIG. 13 is a front-view illustration of the top plate of FIG. 12.
Figure 14:
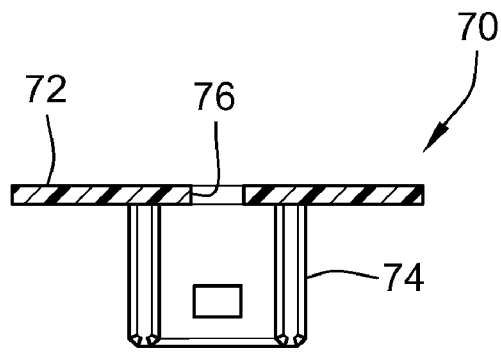
FIG. 14 is a side-view illustration of the top plate of FIG. 12, taken in partial cross-section along line E-E of FIG. 13.

The bottom plate 60 has a central aperture 67 with a generally circular geometry that is configured to receive and pass therethrough slotted, semicircular anchoring bills 74 (see FIGS. 12-14) that project generally orthogonally from a forward face of the top plate base 72. When the safety device 10 is in a deactivated state, which may be seen, for example, in FIG. 1, each anchoring bill 74 also passes through a complimentary quasi-circular, crescent-shaped opening 86 in the base 84 of the needle holder plate 80. At this time, the anchoring bills 74 are cooperatively configured to partially circumscribe the threaded female hub 82 of the needle holder plate 80. In a similar regard, when the safety device 10 is in the deactivated state, the top plate 70 presses against and pins the needle holder plate 80 between the top and bottom plates 70, 60 such that the female luer hub 82 portion of the needle holder plate 80 passes through the central aperture 67 in the bottom plate 60. The top plate 70 and, thus, the needle holder plate 80 are retained in the deactivated position through a locking engagement between the anchoring bills 74 and an actuator plate 90, which is illustrated separately in FIGS. 23 and 24.

Turning next to FIGS. 20 and 22, the bottom plate 60 has a pair of opposing, L-shaped clamps 68 that project generally orthogonally from the forward or outer surface of the base 61. In the example illustrated in FIG. 20, the clamps 68 are integrally molded with the bottom plate 60, and are mirror images of one another. The two clamps 68 cooperatively form a channel therebetween, intended for inseparably mounting the actuator plate 90 to the bottom plate 60 and, thus, the adapter 30. By way of explanation, each L-shaped clamp 68 engages an opposing side of the actuator plate 90, pinning the plate 90 between the clamps 68, as can be seen in FIG. 1. Through this engagement, the actuator plate 90 is hinged to the front plate 60 to slide transversely with respect to the adapter body 32 along the major axis thereof (e.g., left-to-right with respect to FIG. 1), but is restricted from any longitudinal movement along the central axis of the body 32 or lateral motion along the minor axis of the body 32 (e.g., up or down with respect to FIG. 1).

Figure 15A:
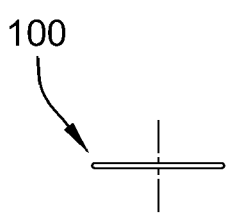
FIG. 15A is a side-view illustration of a first biasing member in accordance with the present invention, shown in a compressed state.
Figure 15B:
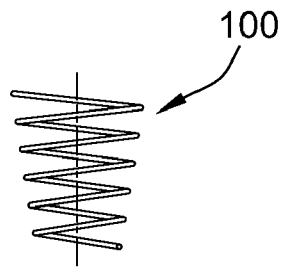
FIG. 15B is a side-view illustration of the first biasing member of FIG. 15A, shown in an expanded state.
Figure 19A:
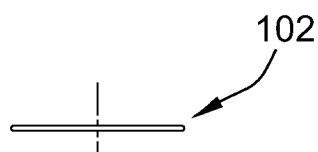
FIG. 19A is a side-view illustration of a second biasing member in accordance with the present invention, shown in a compressed state.
Figure 19B:
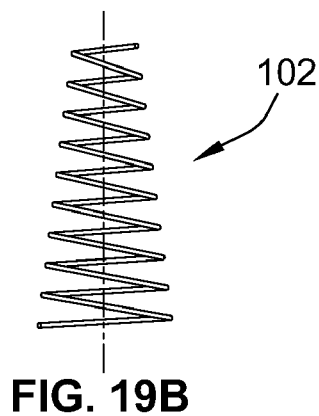
FIG. 19B is a side-view illustration of the second biasing member of FIG. 19A, shown in an expanded state.

Referring back to FIG. 2, the safety device 10 further comprises at least two biasing members, which are represented herein by first and second helical, conical compression springs 100 and 102, respectively. In one exemplary embodiment, the first biasing member 100 is configured to transition from a compressed state, shown in FIG. 15A, wherein the spring 100 is preferably substantially flat due to its tapered, conical shape, to an expanded state, shown in FIG. 15B. Likewise, the second biasing member 102 is configured to transition from a compressed state, shown in FIG. 19A, wherein the spring 102 is preferably substantially flat, to an expanded state, shown in FIG. 19B. The two biasing members 100, 102 provide the retraction control mechanism (i.e., safety device 10) with sufficient force to retract the double-ended hypodermic needle 12 quickly and with precision—e.g., maintaining coaxial alignment between the needle ends 14, 16 and the tubular body 32, and controlling the magnitude of rectilinear travel of the needle 12. In addition, the collaborative interaction of the two biasing members 100, 102 functions to move the two sharp ends 20, 22 of the needle 12 to two different locations within the adapter body 32, both of which are between rigid, relatively impenetrable plastic end plates (i.e., bottom and top plates 60, 70), as depicted, for example, in FIG. 30.

Figure 3:
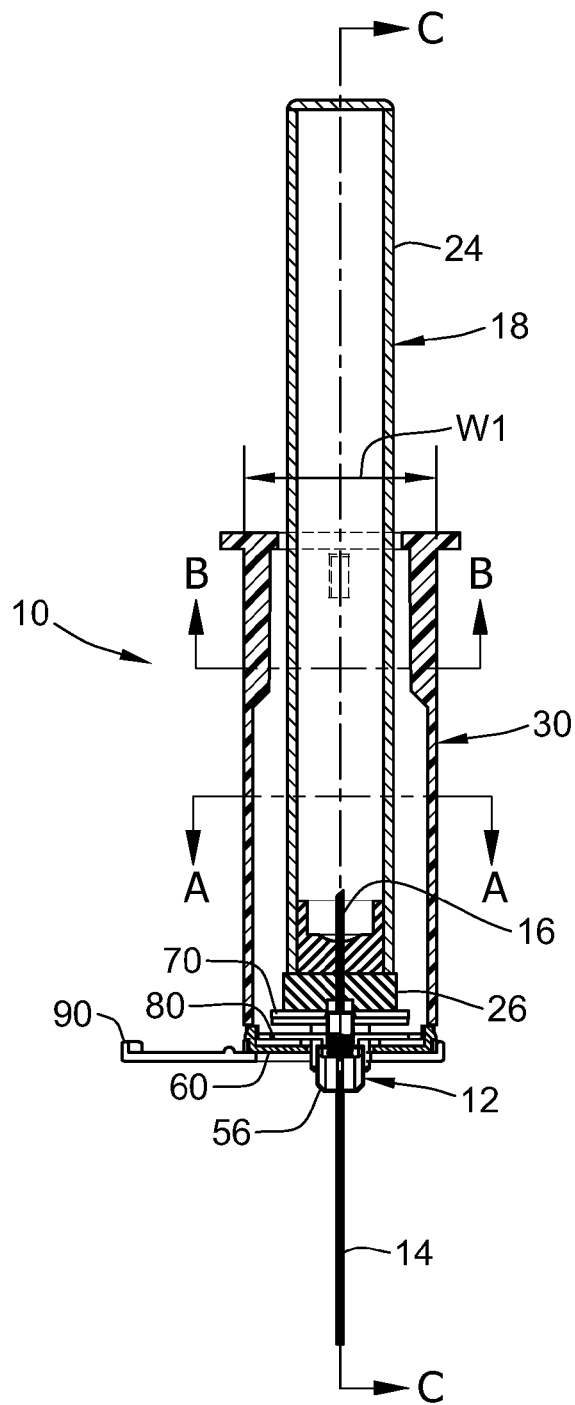
FIG. 3 is a plan-view illustration in partial cross-section of a hypodermic needle safety device in accordance the present invention, including cross-sectional views of an attached double-ended needle, as well as that of an attached fluid-sample collection tube.

In the embodiment illustrated in FIGS. 3 and 6, the top plate 70 selectively anchors the hypodermic needle 12 to the base of the holder 30 against the force of the first and second compression springs 100, 102. When the top plate 70 is secured at the distal end of the adapter body 32—e.g., through locking engagement between the anchoring bills 74 and actuator plate 90, the top plate 70 compresses and pins the first, proximal spring 100 between the top plate 70 and needle holder plate 80. This same locking engagement also acts to compress and pin the second, distal spring 102 between the bottom plate 60 and needle holder plate 80.

In contradistinction, when the actuator plate 90 is activated, as described below, the top plate 70 is released and biased toward the proximal end of the adapter body 32 via the expanding first and second biasing members 100, 102. In other words, the top plate is forced rearward with respect to the adapter body 32 (e.g., toward the top of FIG. 3 or 6) via serial engagement with the first spring 100, needle holder plate 80, second spring 102, and bottom plate 60. Upon completion of the retraction, the top plate 70 irreversibly locks with the adapter body 30 (e.g., via flexible detents 46, 48) and obstructs the proximal circular opening 36 of the tube 32, preventing access to the retracted, proximal end 16 of the double-ended needle 12.

In the illustrated embodiment, the diameter of the rigid, circular top plate base 72 is smaller than the distance between the first and second diametral internal ribs 52, 54 (also referred to herein as "barriers") at the proximal end of the holder tube 32, but is larger than the proximal circular opening 36 of the adapter 30. The thickness of the top plate base 72 is approximately 0.03 inches (0.08 cm), and the margins are preferably straight and smooth and have enough clearance to permit linear ascending movement along the interior of the tube body 32. The top plate 70 has a central hole 76 (FIGS. 13 and 14) defined through the base 72. The central hole 76 is intended to permit the second, proximal end 16 of the double-ended hypodermic needle 12 to pass through the top plate 70 (e.g., allowing for puncturing engagement with the rubber stopper 26 of the vacuum tube 18, as seen in FIG. 3). In the example illustrated in FIG. 13, the hole 76 has a generally square shape that allows, for example, rotation of the plate 70 for engagement and alignment with other components.

Figure 23:
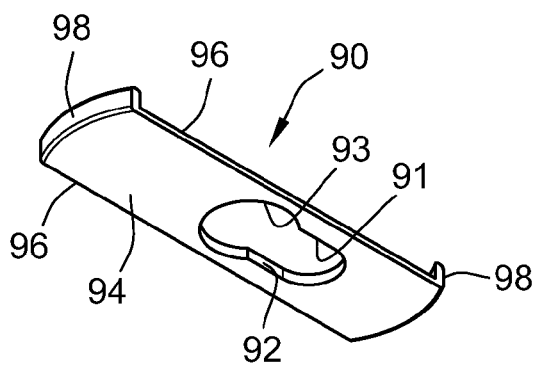
FIG. 23 is a perspective-view illustration of an exemplary actuator plate in accordance with the present invention.
Figure 24:
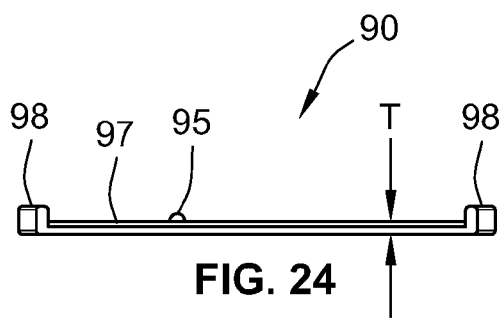
FIG. 24 is a side-view illustration of the actuator plate of FIG. 23.

As previously noted, two symmetrical, semicircular anchoring bills 74 project from a forward/bottom face of the top plate base 72. The outer surface of each anchoring bill 74 is provided with a transverse anchoring notch 78 that is configured to lock the top plate 70 to the actuator plate 90. In particular, according to FIGS. 3 and 6, when the safety device 10 is in the deactivated state, the anchoring bills 74 pass through the crescent-shaped openings 86 in the needle holder plate base 84, the central aperture 67 in the bottom plate base 61, and an oblong, dual-diameter slot 92 in the actuator plate 90, which is best seen in FIG. 23. In this example, the diameter D1 of the semicircular anchoring bills 74 (FIG. 13) is (1) slightly smaller than the diameter D3 of a wide, circular segment 93 (FIG. 29) of the oblong slot 92, to enable the free end portions of the bills 74 to pass through the actuator plate 90, and (2) larger than the diameter D2 of the narrow, circular segment 91 (FIG. 29), to allow mating engagement of the anchoring bills 74 with the actuator plate 90 along opposite edges of the slot 92. By way of clarification, and not limitation, the anchoring notches 78 receive opposite edge portions of the narrow segment 91 of the slot 92 to latch the bills 74 to the actuator plate 90, and thus to the bottom plate base 61, while permitting transverse sliding movement of the actuator plate 90. When the actuator plate 90 is operatively engaged with the anchoring bills 74, the top plate 70 is restricted from ascending axial movement toward the proximal end of the adapter 30. The anchoring bills 74 can be unlatched from the actuator plate 90 by sliding the actuator plate 90 transversely with respect to the adapter 30 (e.g., left to right as viewed in FIG. 3), bringing the wide segment 93 of the slot 92 into register with the bills 74, thereby permitting upward movement of the top plate 70 by the upward force applied to the top plate 70 by the first and second biasing springs 100, 102.

Figure 26:
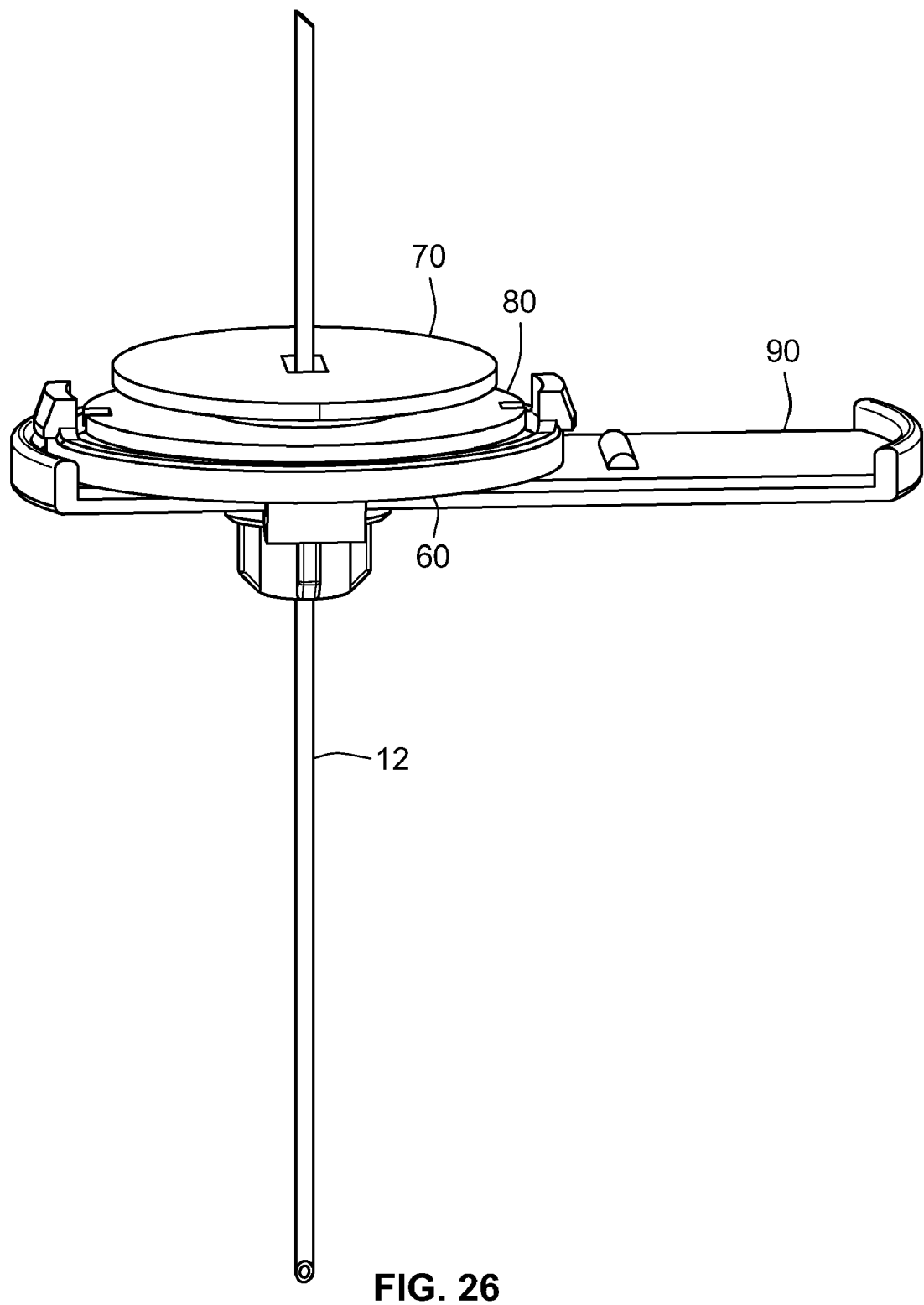
FIG. 26 is a perspective-view illustration of an exemplary retraction control module in accordance with the present invention.

Referring briefly to both FIGS. 3 and 26, the inseparable actuator plate 90, installed on the bottom plate 60 of the holder 30, selectively locks (1) the first biasing member 100, (2) the needle holder plate 80, (3) the second biasing member 102, and (4) the top plate 70, to the bottom plate 60 to form a secure and compact assembly.

The actuator plate 90 preferably comprises a generally rectangular, planar body 94 with rounded ends and integrally molded functional features. The height H2 of the actuator plate body 94 (FIG. 29) is preferably smaller than the height H1 of the adapter tube 32 (FIG. 6). The thickness T of the actuator plate body 94 (FIG. 24) is designed to snugly fit the plate 90 in the channel formed by the two molded L-shaped clamps 68 of the bottom plate 60. The opposing long margins 96 of the actuator plate body 94 have chamfered edges 97 that compliment and slide along a sloping forward geometry of the L-shaped clamps 68, which eases pressing of the actuator plate 90 through the clamps 68 into the channel formed between the two clamps 68. Once engaged, the actuator plate 90 can only move laterally (e.g., left to right as viewed in FIG. 3), and cannot be disengaged or removed from the bottom plate 60 or the holder tube 32. The laterally offset short margins 98 have raised, rounded edges that are elevated and textured to provide a surface to move the plate back and forth in a lateral direction on either side, along the bottom plate of the holder. An added benefit of the raised edges is that once engaged, the tubular body 32 limits the transverse movement of the actuator plate 90 so that it can only be pushed until one of the raised edges 98 contacts a side of the adapter 30.

Figure 27:
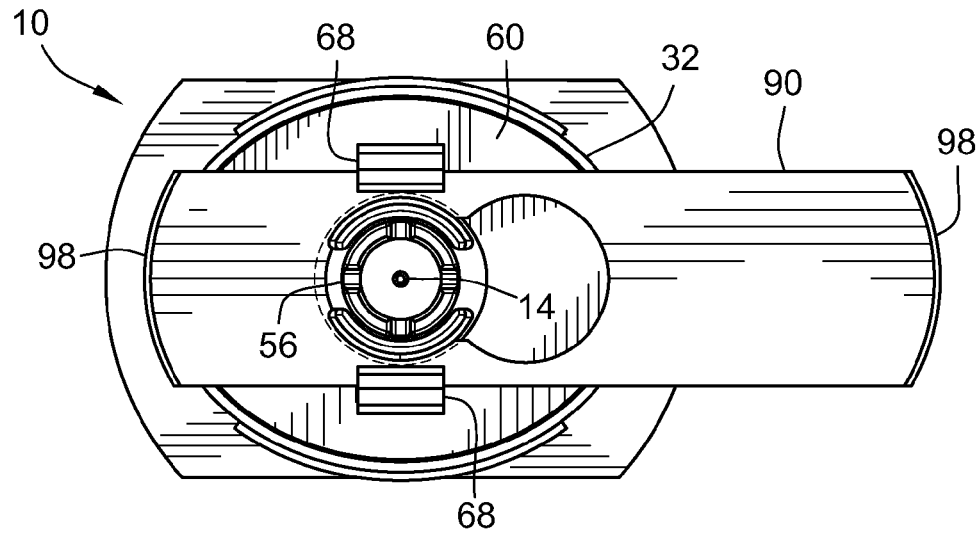
FIG. 27 is a front-view illustration of an exemplary hypodermic needle safety device in accordance with the present invention, showing an actuator plate in a first position and one end of a double-ended hypodermic needle extending from a distal end of the safety device.
Figure 28:
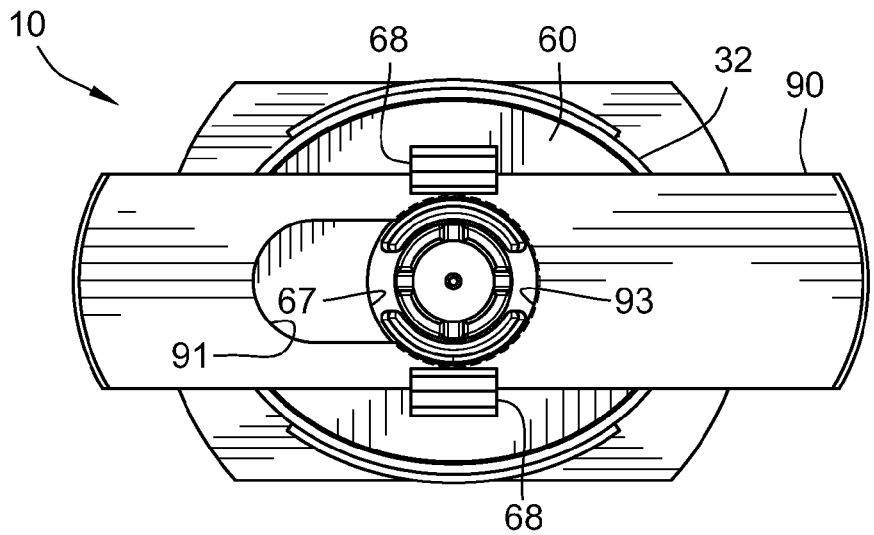
FIG. 28 is a front-view illustration of the safety device of FIG. 27, showing the actuator plate in a second position and the hypodermic needle retracted into a protective adapter.
Figure 29:
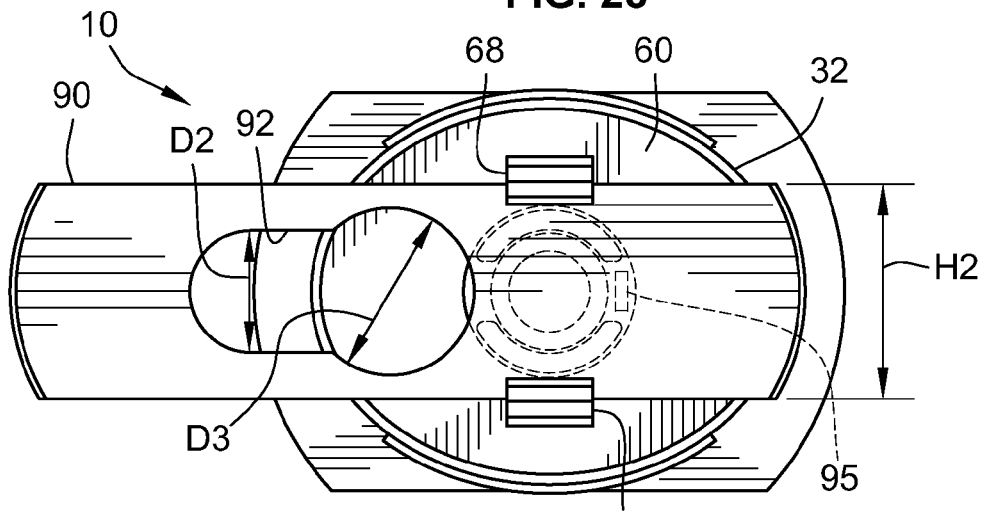
FIG. 29 is a front-view illustration of the safety device of FIG. 27, showing the hypodermic needle in a fully retracted position within the protective adapter and the actuator plate in a third position irreversibly closing a distal opening in the protective adapter.

In the illustrated embodiment of FIGS. 27-29, the wide segment 93 of the oblong slot 92 has a circular geometry coincident with and identical to the central aperture 67 of the bottom plate 60. At the level of the actuator plate 90, the anchoring bills 74 of the top plate 70 have notches 78 that lockably mate with the narrow segment 91 when the actuator plate 90 is pushed off-center (e.g., to the left as viewed in FIG. 3) until the raised edge of the short margin 98 closest to the narrow segment 91 contacts the holder tube 32. When the narrow segment 91 is operatively aligned with the central aperture 67 of the bottom plate 60, an inwardly-projecting detent 95 (FIG. 25) selectively abuts the outer perimeter of tubular body 32 distal end, thereby preventing inadvertent movement of the actuator plate 90 without an active effort to unlock the same by an operator. When the actuator plate 90 is shifted to close off the aperture 67, the same inwardly-projecting detent 95 also acts to engage the inner periphery of the bottom plate aperture 67, thereby preventing reverse travel of the actuator plate 90.

The exemplary biasing members—i.e., compression springs 100 and 102 of FIGS. 15A-15B and 19A-19B, respectively—preferably each have 6-10 circular coils of non-uniform diameter such that when the springs 100 and 102 are in a fully compressed state (respectively shown in FIGS. 15A and 19A) each coil fits inside the circumference of the adjacent larger coil so that the compressed springs are flat. That is, the springs do not have any significant solid length or vertical height dimension—i.e., the thickness of the fully compressed spring is no larger than the diameter of the single wire used to make the spring. In one embodiment, the springs 100, 102 expand in a conical or tapered fashion to the length of approximately 2.6 inches (6.6 cm) to generate an expanding force of approximately 1.5 pounds or more and elevate the various plates as required to retract the needle 12. Another desirable feature of these springs is a single specific apical direction of expansion that requires their specific positioning in the device.

Referring back to FIG. 2, the first, proximal spring 100 has a larger, proximally oriented outer diameter D4 of approximately 0.75" (1.91 cm.), a smaller, distally oriented outer diameter D5 of approximately 0.45" (1.14 cm.), a wire diameter of approximately 0.03" (0.08 cm.), and a free length of approximately 1.0 in (2.54 cm.). In a similar regard, the second, distal spring 102 has a smaller, proximally oriented outer diameter D6 of approximately 0.5" (1.3 cm.), a larger, distally oriented outer diameter D7 of approximately 0.8" (2 cm.), a wire diameter of approximately 0.03" (0.08 cm.), approximately five total active coils, and a free length of approximately 1.85" (4.7 cm.). Such springs provide a force of approximately 1 to 1.5 lbs depending on the exact dimensions and materials. A weaker spring can be made by keeping all the dimensions the same, but reducing the wire diameter.

In the illustrated embodiments, the longer of the two biasing members—e.g., the second, distal spring 102 in the exemplary embodiments of FIGS. 2 and 7—is operatively oriented to retract the longer of the two needle ends—e.g., the distal, puncturing end 14 in the illustrated embodiment—into the holder tube 30, ensuring full retraction of the distal sharp tip 20. The base of the second spring 102 (i.e., the larger, distally oriented outer diameter segment) may be placed directly on the bottom plate 60, abutting a rearward-facing surface thereof. The apex of the second spring 102 (i.e., the smaller, proximally oriented outer diameter segment) encircles the female luer hub 82 of the needle holder plate 80 and, when in the deactivated state, the two semicircular anchoring bills 74 of the top plate 70 that enclose the female luer hub 82.

In the fully retracted state, the needle holder plate 80 rests between the expanded first and second biasing members 100, 102, having retracted the puncturing end 14 of the needle 12 into the rigid holder body 32. The internal, generally oval cross-section of the tubular body 32 (i.e., the first longitudinal cross-section) permits axial movement of the oval needle holder plate 80 within the distal portion of the adapter 30 until the puncturing end 14 of the needle 12 is fully retracted under the expanding force of the second biasing spring 102. The diametral internal ribs 52, 54 in the proximal portion of the adapter 30 provide an effective circular internal configuration (i.e., the second longitudinal cross-section) that continues through the proximal end of the holder tube 32. This configuration permits the circular top plate 70 to travel the entire length of the holder tube 32 from the fully-advance distal end to the fully-retracted proximal end of the adapter 30, while the oval needle holder plate 80 is stopped at a preselected location between the two ends of the adapter 30 by engagement with the internal ribs 52, 54.

The base of the first spring 100 (i.e., the larger, proximally oriented outer diameter segment) may be placed directly against the top plate 70, abutting the forward-facing surface thereof, circumscribing the semicircular anchoring bills 74 of the top plate 70. The apex of the first spring 102 (i.e., the smaller, distally oriented outer diameter segment) abuts a rearward-facing surface the needle holder plate 80. In this arrangement, the proximal spring 100 is partially stabilized by the sample-output end 16 of the needle 12. The proximal spring 100 exerts sufficient pressure on the top plate 70 to displace the plate 70 past the detents 46, 48 and lock the plate 70 at the circular opening 36.

In some applications of the present invention, the end user is provided the safety device 10 ready for use with the actuator plate 90 in a deactivated and locked position (also referred to herein as "first position"), as may be seen, for example, in FIG. 27. It may be desirable that one end of the actuator plate 90, such as the raised, rounded edge of the left-most short margin 98 in FIG. 27, contact with the side of the holder tube 32. When in the deactivated state, the internally threaded female luer hub 82 of the needle holder plate 80 is at the proximal end of the adapter 30, sufficiently accessible for receiving the connector 56 of the hypodermic needle 12. For instance, the female luer hub 82 is concentrically oriented within and visible through the central aperture 67 of the bottom plate 60 at the end of the holder tube 32. In this location, the double-ended hypodermic needle 12 can be easily screwed to the holder plate 80 and, thus, the safety device 10, such that a sufficient length of the sample-intake end 14 is externally oriented for collection of fluid samples. By way of explanation, and not limitation, a healthcare worker can remove a safety cap (not shown) on the proximal end 16 of the double-ended needle 12, insert the connector 56 into the female luer 82, rotate the connector 56 to threadably lock the needle 12 to the needle holder 80, and remove the needle shield covering the distal end 14 of the needle 12 to expose the puncturing end 22. The front-end view of the safety device 10 in FIG. 27 shows the attached needle 12 in the center, protruding axially from the distal end of the adapter body 32.

Continuing with the above example, once the needle 12 is properly attached to the safety device 10, the healthcare worker inserts the puncturing end 22 of the needle 12 into a patient's vein and attaches a fluid-sample collection device to the sample-output end 16 (e.g., the vacuum tube 18 of FIG. 1 is inserted in through the proximal end opening 36 of adapter 30, and pushed onto the second sharp tip 22 of the needle 12).

After all the required samples are collected, the collection device is withdrawn and the needle 12 is pulled out of the vein. The user then presses on the textured projecting margin of the actuator plate 90—i.e., the raised, rounded edge of the right-most short margin 98 in FIG. 27. Due to the arrangement of the safety device 10, there is only one pushable end of the actuator plate 90, as the opposing end is restricted from moving by the tubular body 32. Upon pressing the actuator plate 90, the plate 90 shifts the narrow segment 91 off center (e.g., to the left in FIG. 28), and centrally aligns the wider segment 93 with the bottom plate central aperture 67 (also referred to herein as "second position"), as seen in FIG. 28. This releases the semicircular anchoring bills 74 of the top plate 70 and, in so doing, allows the compressed biasing springs 100, 102 to expand, whereby the safety device instantly draws the needle 12 inside the tubular body. In addition, the top plate 70 ascends to the proximal end of the adapter 30 to secure the opening 36. During transit, the top plate 70 displaces and passes over the top of the detents 46, 48. Once the top plate 70 is immediately adjacent the opening 36, reverse travel is restricted because the plate 70 is locked between the rim of the opening 36 and the detents 46, 48.

Continued pushing on the plate 90 will shift the wider, semicircular segment 93 off center (e.g., to the left in FIG. 28) with respect to the bottom plate central aperture 67 (also referred to herein as the "third position"), which may be seen in FIG. 29. The additional push on the actuator plate 90 closes the opening 67. It may be desirable that the other end of the actuator plate 90, such as the raised, rounded edge of the right-most short margin 98 in FIG. 29, contact with the side of the holder tube 32 to limit transverse movement of the actuator plate 90. The actuator plate detent 95 (shown hidden in FIG. 29), which now sits in the wider, semicircular segment 93 of the oblong slot 92, prevents reverse travel of the actuator plate 90. The device 10 is thus permanently locked and disabled. There is no potential that either end 20 or 22 of the needle 12 can inadvertently puncture or prick another person. The device should therefore not be classified as a sharp device which would otherwise be destined for a sharps container. Instead, the post-use safety device may be discarded in a standard biological waste ("red bag"), thereby reducing the cost of disposal.

Turning next to FIG. 30, wherein like reference numbers are used to indicate like structure, a plan-view illustration of an exemplary hypodermic needle safety device 10' is shown in accordance with an alternate embodiment of the present invention. The safety device 10' is depicted with an outer protective adapter 30' broken away in partial cross-section to show a double-ended hypodermic needle 12 encased within the adapter 30'. The safety device 10' is functionally similar to the safety device 10 of FIG. 1. In the alternative embodiment of FIG. 30, however, the adapter 30' is modified from the adapter 30 of FIG. 1 to include two or more internal, elongated rails 52' and 54' that extend the entire length of the adapter body 32'. In the exemplification illustrated in FIG. 30, the rails 52', 54' are laterally offset from one another, protruding inward from antipodal points of the major axis of the tubular body oval-shaped cross-section.

The rails 52', 54' are intended to offer additional structural integrity for the adapter body 32'. The rails 52', 54' are also configured to engage with complimentary notches 81' and 83' on the margins of a needle holder plate 80' to provide controlled movement and proper alignment of the plate 80' during retraction thereof. In particular, when the needle holder plate 80' is biased from the distal end toward the proximal end of the adapter 32' (i.e., via expansion of compression spring 102), the longitudinal progress of the plate 80' is halted at a predetermined retraction limit by a widened segment (or shoulder) 53' and 55' of each rail 52' 54'. In the illustrated embodiment, for example, the distance between the two rails 52', 54' at the distal end of the body 32' is sufficiently wide to allow free, unfettered movement of the needle holder plate 80 in the longitudinal direction. However, the shoulders 53', 55' sufficiently reduce the distance between the two rails 52', 54' such that the needle holder plate 80' will engage the shoulders 53', 55' along a rearward face of the base 81', restricting any further longitudinal travel.

In contrast, the narrower, circular geometry of the top plate 70 allows the plate 70 to continue its full ascent to close the adapter opening 36' and safely secure the needle 12 in the adapter 30'. In other words, the diameter of the top plate base 72 is smaller than the distance between the two widened, shoulder segments 53', 55'; thus, longitudinal travel of the top plate 70 is unimpeded by the shoulders 53', 55'. Optionally, the top plate 70 may also be fabricated with complimentary notches that are shaped, sized, and oriented to engage the rails 52', 54' to proper alignment of the plate 70 during retraction thereof.

In another alternative embodiment, the adapter body and bottom plate may be formed as a single unitary part. The open proximal end of the unitary part may be used to insert and assemble the other interior parts, with the top plate being deformable to allow it to be pushed through a smaller opening.

The present invention also provides a method of assembling a protective device for securely stowing a double sharp-ended hypodermic needle. In some embodiments of the present invention, the protective device includes, but is certainly not limited to: (1) a tubular adapter, (2) an actuator plate, (3) a bottom plate, (4) a first compression spring, (5) a needle holder plate, (6) a second compression spring, and (7) a top plate. For efficient and economic assembly, a moving rotary or linear platform is provided with nests of adapter configuration and an axially, standing vertical steel rod of uniform diameter. The first step includes squeezing and irreversibly engaging an actuator plate to a bottom plate to begin the placement of feeding components on the steel rod. The components enumerated above are then sequentially and co-axially inserted onto the rod in the nest. Once all of the components are fed, a vertical pressure press assembles all the components, and a simultaneous push of the actuator plate locks the various components in a compressed, deactivated state. Insertion engagement of the erect tubular shell with solvent bonding completes the assembly of the adapter.

While the present invention has been described with reference to one or more particular embodiments, those familiar with the art to which this invention relates will recognize various alternative designs and embodiments for practicing the invention within the scope of the appended claims.

The invention claimed is:

1. A safety device for selectively stowing a needle with a first and second sharp ends, the safety device comprising:
    an elongated body defining a longitudinally oriented channel with a first channel opening spaced from a second channel opening;
    a needle holder configured to mate with and attach to the needle, wherein said needle holder is movably arranged at least partially in said channel to move between a first location, in which the first sharp end of the needle projects at least partially from said first channel opening, and a second location, in which both the first and second sharp ends of the needle are enclosed within said body between said first and second openings;
    a top plate movably arranged with respect to said elongated body to transition from a first orientation, in which said top plate is distal from said second channel opening, and a second orientation, in which said top plate is proximal to and at least partially obstructs said second channel opening; and an actuator plate movably attached to said elongated body to selectively transition between a first position, in which said actuator plate retains said needle holder in said first location and said top plate in said first orientation, a second position, in which said needle holder is moved to said second location and said top plate is moved to said second orientation, and a third position, in which said actuator plate fully obstructs said first channel-opening.

2. The safety device of claim 1, further comprising a first biasing member engaged with said needle holder and configured to selectively bias said needle holder to said second location when said actuator plate is moved to said second position.

3. The safety device of claim 2, further comprising a second biasing member engaged with said top plate and configured to selectively bias said top plate to said second orientation when said actuator plate is moved to said second position.

4. The safety device of claim 3, wherein said first and second biasing members are springs retained in compressed states between said actuator plate and said top plate via said actuator plate when in said first position.

5. The safety device of claim 4, wherein said first and second biasing members are substantially flat when in respective compressed states.

6. The safety device of claim 1, further comprising a bottom plate operatively attached to said elongated body and configured to partially close off said first channel opening.

7. The safety device of claim 6, wherein said elongated body defines a plurality of windows, and wherein said bottom plate includes a plurality of projections each configured to mate with a respective one of said windows and thereby rigidly attach said bottom plate to said elongated body.

8. The safety device of claim 6, wherein said bottom plate includes first and second opposing clamps cooperatively configured to slidably mount said actuator plate to said bottom plate.

9. The safety device of claim 6, wherein said bottom plate defines an aperture configured to pass therethrough the first sharp end of the needle when said needle holder is in said first location.

10. The safety device of claim 9, wherein said actuator plate includes a detent configured to selectively engage the perimeter of said bottom plate aperture when said actuator plate is in said third position to thereby restrict reverse travel of said actuator plate.

11. The safety device of claim 1, wherein said elongated body further comprises a plurality of internal barriers configured to obstruct movement of said needle holder and thereby retain said needle holder at said second location.

12. The safety device of claim 1, wherein said elongated body further comprises a plurality of internal longitudinally-elongated rails configured to engage with complimentary notches formed in said needle holder, each of said rails including a shoulder configured to obstruct movement of said needle holder and thereby retain said needle holder at said second location.

13. The safety device of claim 1, wherein said actuator plate includes a first raised edge configured to engage said elongated body and thereby restrict movement of said actuator plate in a first direction, and a second raised edge configured to engage said elongated body and thereby restrict movement of said actuator plate in a second direction different from said first direction.

14. The safety device of claim 1, wherein said top plate includes a plurality of anchoring bills configured to engage with said actuator plate when in said first position and thereby retain said top plate in said first orientation.

15. The safety device of claim 14, wherein each of said anchoring bills defines an anchoring notch configured to latch to a respective side of said actuator plate.

16. The safety device of claim 14, wherein said anchoring bills protrude generally orthogonally from a base of said top plate, each passing through a complimentary opening in a base of said needle holder when said top plate is in said first orientation.

17. The safety device of claim 1, wherein said top plate defines a hole configured to pass therethrough the second sharp end of the needle when said needle holder is at said first location.

18. A protective device for securely stowing a double sharp-ended hypodermic needle having a puncturing end for piercing tissue, a distributing end for piercing a fluid-sample collection device, and a connector, the protective device comprising:

a tubular holder defining therein a longitudinally elongated channel with a distal channel opening longitudinally-spaced from a proximal channel opening;

a needle holder plate with a female luer configured to receive and attach to the needle connector, wherein said needle holder is movably arranged in said channel to transition from a distal location, in which the puncturing end of the hypodermic needle projects from said distal channel opening, to a proximal location, in which both the puncturing and distributing ends of the needle are enclosed within said holder between said proximal and distal openings;

a first spring abutting said needle holder plate and configured to selectively bias said needle holder plate from said distal location to said proximal location; a top plate movably arranged in said channel to transition from a distal orientation, in which said top plate is distal from said proximal channel opening, and a proximal orientation, in which said top plate is proximal to and substantially obstructs said proximal channel opening;

a second spring abutting said top plate and configured to selectively bias said top plate from said distal orientation to said proximal orientation; and an actuator plate slidably attached to the distal end of said tubular holder to selectively transition: from a first position, in which said actuator plate retains said needle holder in said distal location, said top plate in said distal orientation, and said first and second springs in compressed states, to a second position, in which said actuator plate releases said needle holder, said top plate, and said first and second springs such that said first spring biases said needle holder to said proximal location and said second spring biases said top plate to said second orientation, and to a third position, in which said actuator plate fully obstructs said distal channel opening.

19. The protective device of claim 18, wherein said top plate, when in said distal orientation, latches to said actuator plate, when in said first position, and presses against said needle holder plate thereby retaining said needle holder plate in said first location.

20. The protective device of claim 19, further comprising a bottom plate rigidly mounted to said tubular holder and partially closing off said distal channel opening, wherein said first spring is disposed between said bottom plate and said needle holder plate, and said second spring is disposed between said needle holder plate and said top plate.

21. The protective device of claim 18, wherein a distal portion of said tubular holder has a first longitudinal cross-section, and a proximal portion of said tubular holder has a second longitudinal cross-section different from said first longitudinal cross-section.

22. The protective device of claim 21, wherein said first longitudinal cross-section provides unfettered longitudinal movement of both said needle holder plate and said top plate, whereas said second longitudinal cross-section restricts movement of said needle holder plate to said second location but provides unfettered longitudinal movement of said top plate.

23. The protective device of claim 21, wherein said first longitudinal cross-section and a base of said needle holder have a complimentary generally-oval shape, whereas said second longitudinal cross-section and a base of said top plate have a complimentary generally-circular shape.

24. The protective device of claim 18, wherein moving said actuator plate to said third position locks the double sharp-ended hypodermic needle inside said tubular holder between said top plate and said actuator plate.

25. The protective device of claim 18, wherein said tubular holder further comprises a plurality of rails each longitudinally-elongated within said channel and projecting inward to engage with a complimentary notch formed in said needle holder plate thereby aligning said needle holder plate for linear movement inside the channel.

26. The protective device of claim 25, wherein each of said rails includes a widened segment configured to engage said needle holder plate during retraction thereof and thereby retain said needle holder at said second location.

27. The protective device of claim 18, wherein said tubular holder further comprises a plurality of detents each projecting inward within said channel at a proximal end of said tubular holder, said plurality of detents being configured to deflect outward during transition of said top plate to said proximal orientation and to lock said top plate in said proximal orientation immediately adjacent said proximal channel opening.

28. The protective device of claim 18, wherein the hypodermic needle is coaxially aligned with the tubular holder.

29. The protective device of claim 18, wherein said tubular holder further comprises a pair of integral flanges projecting transversely from opposing sides of said tubular holder.

30. A method of retracting and safely stowing a double sharp-ended hypodermic needle mounted to a needle holder moveable with respect to an adapter body of a safety device, the method comprising:
    moving an actuator plate from a first position to a second position, whereby: a first biasing member forces the needle holder to an intermediate location within the adapter body such that both sharp ends of the needle are inside the adapter body spaced from distal and proximal open ends thereof, and a second biasing member forces a top plate to a proximal end of the adapter body thereby substantially obstructing the proximal open end; and
    moving the actuator plate from the second position to a third position, whereby the actuator plate fully obstructs the distal open end of the adapter body such that both sharp ends of the needle are concealed within the adapter body, is held vertically straight in the axis of the holder tube preventing the needle to puncture the wall of holder tube by obliquity.

31. A fluid-sample collection device, comprising:
    a hypodermic needle having a sharp puncturing end longitudinally spaced from a sharp distributing end, and a connector intermediate said puncturing and distributing ends;
    a tubular adapter having a hollow body defining a channel with a distal opening longitudinally-spaced from a proximal opening;
    a first biasing member;
    a second biasing member;
    a top plate having a base with a first diameter smaller than a smallest dimension of said channel and larger than a smallest dimension of said proximal channel opening, said top plate having anchoring means projecting from said base, wherein said top plate is movably arranged in said channel to transition from a distal orientation, in which said top plate is adjacent said distal channel opening, and a proximal orientation, in which said top plate is adjacent and substantially obstructing said proximal channel opening;
    a needle holder releasably attached to said needle connector, said needle holder having a base defining a plurality of openings each configured to pass therethrough a respective one of said top plate anchoring means, wherein said needle holder is movably arranged in said channel to transition from a distal location, in which said puncturing end of said hypodermic needle projects from said distal channel opening, to a proximal location, in which both said puncturing and distributing ends of said needle are enclosed within said adapter between said proximal and distal openings;
    a bottom plate rigidly mounted to said tubular adapter and partially closing off said distal channel opening, said bottom plate having a base defining an aperture configured to pass therethrough said top plate anchoring means and said puncturing end of said needle; and
    an actuator plate slidably attached to said bottom plate to move from a first position, in which said top plate anchoring means engage said actuator plate thereby retaining said needle holder in said distal location and said top plate in said distal orientation, to a second position, in which said top plate anchoring means disengage said actuator plate such that said first biasing member biases said needle holder to said proximal location and said second biasing member biases said top plate to said second orientation, and to a third position, in which said actuator plate fully obstructs said distal channel opening.

32. The fluid-sample collection device of claim 31, wherein said actuator plate includes a planar body defining an oblong slot with a narrow segment and a wide segment.

33. The fluid-sample collection device of claim 32, wherein said narrow segment of said oblong slot aligns with said top plate and attaches to said anchoring means when said actuator plate is in said first position, and said wide segment aligns with said top plate and disengages said anchoring means when said actuator plate is in said second position.

34. A retraction control module for a blood sampling device having a needle with first and second sharp ends, the retraction control module comprising:
    a needle holder configured to mate with and attach to the needle and adapted to be movably arranged in a channel to move between a first location, in which the first sharp end of the needle projects at least partially from a first channel opening, and a second location, in which both the first and second sharp ends of the needle are enclosed between said first channel opening and a second channel opening;

a top plate adapted to be movably arranged with respect to said channel to transition from a first orientation, in which said top plate is distal from said second channel opening, and a second orientation, in which said top plate is proximal to and at least partially obstructs said second channel opening;

a bottom plate configured to partially close off said first channel opening;

an actuator plate movably attached to said bottom plate to selectively transition between a first position, in which said actuator plate retains said needle holder in said first location and said top plate in said first orientation, a second position, in which said needle holder is moved to said second location and said top plate is moved to said second orientation, and a third position, in which said actuator plate fully obstructs said first channel opening;

a first biasing member engaged with said needle holder and configured to selectively bias said needle holder to said second location when said actuator plate is moved to said second position; and a second biasing member engaged with said top plate and configured to selectively bias said top plate to said second orientation when said actuator plate is moved to said second position.

35. The retraction control module of claim 34 in which said first biasing member is located between said bottom plate and said needle holder, said second biasing member is located between said needle holder and said top plate, and said top plate, said needle holder and said bottom plate are all held closely together, compressing both biasing members, by said actuator plate engaging said top plate.

* * * * *